(12) United States Patent
Demarais et al.

(10) Patent No.: US 7,753,870 B2
(45) Date of Patent: Jul. 13, 2010

(54) SYSTEMS AND METHODS FOR TREATING OBESITY

(75) Inventors: Denise Marie Demarais, Los Gatos, CA (US); Thomas J. Fogarty, Portola Valley, CA (US); James Gannoe, West Milford, NJ (US)

(73) Assignee: Satiety, Inc., Palo Alto, CA (US)

( * ) Notice: Subject to any disclaimer, the term of this patent is extended or adjusted under 35 U.S.C. 154(b) by 730 days.

(21) Appl. No.: 11/091,023

(22) Filed: Mar. 25, 2005

(65) Prior Publication Data

US 2005/0228504 A1 Oct. 13, 2005

Related U.S. Application Data

(60) Provisional application No. 60/556,489, filed on Mar. 26, 2004, provisional application No. 60/569,037, filed on May 10, 2004.

(51) Int. Cl.
*A61M 5/00* (2006.01)

(52) U.S. Cl. .......................................... 604/8

(58) Field of Classification Search ..... 623/23.64–23.7; 604/8, 9; 128/898
See application file for complete search history.

(56) References Cited

U.S. PATENT DOCUMENTS

| 2,108,206 A | 2/1938 | Meeker |
|---|---|---|
| 2,508,690 A | 5/1950 | Schmerl |
| 3,372,443 A | 3/1968 | Daddona, Jr. |
| 3,395,710 A | 8/1968 | Stratton et al. |
| 3,986,493 A | 10/1976 | Hendren, III |
| 4,057,065 A | 11/1977 | Thow |
| 4,063,561 A | 12/1977 | McKenna |
| 4,133,315 A | 1/1979 | Berman et al. |
| 4,134,405 A | 1/1979 | Smit |
| 4,198,982 A | 4/1980 | Fortner et al. |
| 4,246,893 A | 1/1981 | Berson |
| 4,258,705 A | 3/1981 | Sorensen et al. |
| 4,311,146 A | 1/1982 | Wonder |
| 4,315,509 A | 2/1982 | Smit |

(Continued)

FOREIGN PATENT DOCUMENTS

EP 0 137 878 A1 4/1985

(Continued)

OTHER PUBLICATIONS

Benjamin, S.B., et al., *A Double-Blind Cross Over Study of the Garren-Edwards anti-Obesity Bubblem* Abstract Submitted to A/S/G/E/ 1987, Georgetown University Hospital and Fairfax Hospital, Washington, D.C. and Fairfax, VA.

(Continued)

*Primary Examiner*—(Jackie) Tan-Uyen T Ho
*Assistant Examiner*—Melanie Tyson
(74) *Attorney, Agent, or Firm*—Fulwider Patton LLP

(57) ABSTRACT

Methods and devices for simulating a gastric bypass and reducing the volume of the stomach involve placing a tubular liner along the lesser curve of the stomach cavity. Also, methods and devices for slowing gastric emptying involve placing valves within the stomach cavity near the gastro-intestinal junction and/or the pylorus. These methods and devices may prevent a patient from drinking and eating large volumes at one time and from eating slowly all day.

11 Claims, 13 Drawing Sheets

U.S. PATENT DOCUMENTS

| | | |
|---|---|---|
| 4,343,066 A | 8/1982 | Lance |
| 4,402,445 A | 9/1983 | Green |
| 4,416,267 A | 11/1983 | Garren et al. |
| 4,458,681 A | 7/1984 | Hopkins |
| 4,485,805 A | 12/1984 | Foster, Jr. |
| 4,501,264 A | 2/1985 | Rockey |
| 4,547,192 A | 10/1985 | Brodsky et al. |
| 4,558,699 A | 12/1985 | Bashour |
| 4,592,339 A | 6/1986 | Kuzmak et al. |
| 4,592,354 A | 6/1986 | Rothfuss |
| 4,598,699 A | 7/1986 | Garren et al. |
| 4,607,618 A | 8/1986 | Angelchik |
| 4,610,383 A | 9/1986 | Rothfuss et al. |
| 4,636,205 A | 1/1987 | Steer |
| 4,641,653 A | 2/1987 | Rockey |
| 4,643,169 A | 2/1987 | Koss et al. |
| 4,646,722 A | 3/1987 | Silverstein et al. |
| 4,648,383 A | 3/1987 | Angelchik |
| 4,671,287 A | 6/1987 | Fiddian-Green |
| 4,694,827 A | 9/1987 | Weiner et al. |
| 4,716,900 A | 1/1988 | Ravo et al. |
| 4,723,547 A | 2/1988 | Kullas et al. |
| 4,739,758 A | 4/1988 | Lai et al. |
| 4,744,363 A | 5/1988 | Hasson |
| 4,773,393 A | 9/1988 | Haber et al. |
| 4,790,294 A | 12/1988 | Allred, III et al. |
| 4,795,430 A | 1/1989 | Quinn et al. |
| 4,803,985 A | 2/1989 | Hill |
| 4,841,888 A | 6/1989 | Mills et al. |
| 4,899,747 A | 2/1990 | Garren et al. |
| 4,905,693 A | 3/1990 | Ravo |
| 4,925,446 A | 5/1990 | Garay et al. |
| 4,927,428 A | 5/1990 | Richards |
| 4,969,474 A | 11/1990 | Schwarz |
| 5,037,021 A | 8/1991 | Mills et al. |
| 5,059,193 A | 10/1991 | Kuslich |
| 5,080,663 A | 1/1992 | Mills et al. |
| 5,084,061 A | 1/1992 | Gau et al. |
| 5,112,310 A | 5/1992 | Grobe |
| 5,129,915 A | 7/1992 | Cantenys |
| 5,156,609 A | 10/1992 | Nakao et al. |
| 5,171,233 A | 12/1992 | Amplatz et al. |
| 5,197,649 A | 3/1993 | Bessler et al. |
| 5,220,928 A | 6/1993 | Oddsen et al. |
| 5,222,961 A | 6/1993 | Nakao et al. |
| 5,226,429 A | 7/1993 | Kuzmak |
| 5,234,454 A | 8/1993 | Bangs |
| 5,246,456 A | 9/1993 | Wilkinson |
| 5,248,302 A | 9/1993 | Patrick et al. |
| 5,250,058 A | 10/1993 | Miller et al. |
| 5,254,126 A | 10/1993 | Filipi et al. |
| 5,259,366 A | 11/1993 | Reydel et al. |
| 5,259,399 A | 11/1993 | Brown |
| 5,261,920 A | 11/1993 | Main et al. |
| 5,263,629 A | 11/1993 | Trumbull et al. |
| 5,297,536 A | 3/1994 | Wilk |
| 5,301,658 A | 4/1994 | Zhu et al. |
| 5,306,300 A | 4/1994 | Berry |
| 5,309,896 A | 5/1994 | Moll et al. |
| 5,309,927 A | 5/1994 | Welch |
| 5,327,914 A | 7/1994 | Shlain |
| 5,330,486 A | 7/1994 | Wilk |
| 5,330,503 A | 7/1994 | Yoon |
| 5,331,975 A | 7/1994 | Bonutti |
| 5,334,209 A | 8/1994 | Yoon |
| 5,334,210 A | 8/1994 | Gianturco |
| 5,345,949 A | 9/1994 | Shlain |
| 5,346,501 A | 9/1994 | Regula et al. |
| 5,355,897 A | 10/1994 | Pietrafitta et al. |
| 5,376,095 A | 12/1994 | Ortiz |
| 5,382,231 A | 1/1995 | Shlain |
| 5,403,312 A | 4/1995 | Yates et al. |
| 5,403,326 A | 4/1995 | Harrison et al. |
| 5,411,508 A | 5/1995 | Bessler et al. |
| 5,433,721 A | 7/1995 | Hooven et al. |
| 5,437,291 A | 8/1995 | Pasricha et al. |
| 5,449,368 A | 9/1995 | Kuzmak |
| 5,452,837 A | 9/1995 | Williamson, IV et al. |
| 5,458,131 A | 10/1995 | Wilk |
| 5,465,894 A | 11/1995 | Clark et al. |
| 5,467,911 A | 11/1995 | Tsuruta et al. |
| 5,486,183 A | 1/1996 | Middleman et al. |
| 5,489,058 A | 2/1996 | Plyley et al. |
| 5,503,635 A | 4/1996 | Sauer et al. |
| 5,527,319 A | 6/1996 | Green et al. |
| 5,535,935 A | 7/1996 | Vidal et al. |
| 5,542,949 A | 8/1996 | Yoon |
| 5,549,621 A | 8/1996 | Bessler et al. |
| 5,551,622 A | 9/1996 | Yoon |
| 5,555,898 A | 9/1996 | Suzuki et al. |
| 5,558,665 A | 9/1996 | Kieturakis |
| 5,571,116 A | 11/1996 | Bolanos et al. |
| 5,577,654 A | 11/1996 | Bishop |
| 5,578,044 A | 11/1996 | Gordon et al. |
| 5,582,616 A | 12/1996 | Bolduc et al. |
| 5,584,861 A | 12/1996 | Swain et al. |
| 5,588,579 A | 12/1996 | Schnut et al. |
| 5,601,604 A | 2/1997 | Vincent |
| 5,603,443 A | 2/1997 | Clark et al. |
| 5,607,094 A | 3/1997 | Clark et al. |
| 5,624,381 A | 4/1997 | Kieturakis |
| 5,626,588 A | 5/1997 | Sauer et al. |
| 5,639,008 A | 6/1997 | Gallagher et al. |
| 5,649,937 A | 7/1997 | Bito et al. |
| 5,651,769 A | 7/1997 | Waxman et al. |
| 5,655,698 A | 8/1997 | Yoon |
| 5,662,664 A | 9/1997 | Gordon et al. |
| 5,662,667 A | 9/1997 | Knodel |
| 5,667,520 A | 9/1997 | Bonutti |
| 5,676,659 A | 10/1997 | McGurk |
| 5,676,674 A | 10/1997 | Bolanos et al. |
| 5,685,868 A | 11/1997 | Lundquist |
| 5,690,656 A | 11/1997 | Cope et al. |
| 5,697,943 A | 12/1997 | Sauer et al. |
| 5,707,382 A | 1/1998 | Sierocuk et al. |
| 5,722,990 A | 3/1998 | Sugarbaker et al. |
| 5,728,178 A | 3/1998 | Buffington et al. |
| 5,735,848 A | 4/1998 | Yates et al. |
| 5,749,893 A | 5/1998 | Vidal et al. |
| 5,755,730 A | 5/1998 | Swain et al. |
| 5,766,216 A | 6/1998 | Gangal et al. |
| 5,776,054 A | 7/1998 | Bobra |
| 5,782,844 A | 7/1998 | Yoon et al. |
| 5,788,715 A | 8/1998 | Watson, Jr. et al. |
| 5,792,153 A | 8/1998 | Swain et al. |
| 5,797,931 A | 8/1998 | Bito et al. |
| 5,810,851 A | 9/1998 | Yoon |
| 5,810,855 A | 9/1998 | Rayburn et al. |
| 5,810,882 A | 9/1998 | Bolduc et al. |
| 5,816,471 A | 10/1998 | Plyley et al. |
| 5,820,584 A | 10/1998 | Crabb |
| 5,824,008 A | 10/1998 | Bolduc et al. |
| 5,827,298 A | 10/1998 | Hart et al. |
| 5,833,690 A | 11/1998 | Yates et al. |
| 5,836,311 A | 11/1998 | Borst et al. |
| 5,839,639 A | 11/1998 | Sauer et al. |
| 5,860,581 A | 1/1999 | Robertson et al. |
| 5,861,036 A | 1/1999 | Godin |
| 5,868,141 A | 2/1999 | Ellias |
| 5,868,760 A | 2/1999 | McGuckin, Jr. |
| 5,876,448 A | 3/1999 | Thompson et al. |
| 5,879,371 A | 3/1999 | Gardiner et al. |
| 5,887,594 A | 3/1999 | LoCicero, III |
| 5,888,196 A | 3/1999 | Bonutti |

| | | | | | | |
|---|---|---|---|---|---|---|
| 5,897,534 | A | 4/1999 | Heim et al. | 6,558,400 B2 | 5/2003 | Deem et al. |
| 5,897,562 | A | 4/1999 | Bolanos et al. | 6,561,969 B2 | 5/2003 | Frazier et al. |
| 5,904,147 | A | 5/1999 | Conlan et al. | 6,572,629 B2 | 6/2003 | Kalloo et al. |
| 5,906,625 | A | 5/1999 | Bito et al. | 6,592,596 B1 | 7/2003 | Geitz |
| 5,910,105 | A | 6/1999 | Swain et al. | 6,605,037 B1 | 8/2003 | Moll et al. |
| 5,910,149 | A | 6/1999 | Kuzmak | 6,626,899 B2 | 9/2003 | Houser et al. |
| 5,921,993 | A | 7/1999 | Yoon | 6,632,227 B2 | 10/2003 | Adams |
| 5,927,284 | A | 7/1999 | Borst et al. | 6,663,598 B1 | 12/2003 | Carrillo, Jr. et al. |
| 5,928,264 | A | 7/1999 | Sugarbaker et al. | 6,663,639 B1 | 12/2003 | Laufer et al. |
| 5,935,107 | A | 8/1999 | Taylor et al. | 6,663,640 B2 | 12/2003 | Kortenbach |
| 5,938,669 | A | 8/1999 | Klaiber et al. | 6,675,809 B2 | 1/2004 | Stack et al. |
| 5,947,983 | A | 9/1999 | Solar et al. | 6,682,520 B2 | 1/2004 | Ingenito |
| 5,964,772 | A | 10/1999 | Bolduc et al. | 6,689,062 B1 | 2/2004 | Mesallum |
| 5,964,782 | A | 10/1999 | Lafontaine et al. | 6,692,485 B1 | 2/2004 | Brock et al. |
| 5,972,001 | A | 10/1999 | Yoon | 6,716,222 B2 | 4/2004 | McAlister et al. |
| 5,972,002 | A | 10/1999 | Bark et al. | 6,733,512 B2 | 5/2004 | McGhan |
| 5,976,161 | A | 11/1999 | Kirsch et al. | 6,736,822 B2 | 5/2004 | McClellan et al. |
| 5,980,537 | A | 11/1999 | Ouchi | 6,740,098 B2 | 5/2004 | Abrams et al. |
| 5,993,464 | A | 11/1999 | Knodel | 6,740,121 B2 | 5/2004 | Geitz |
| 5,993,473 | A | 11/1999 | Chan et al. | 6,746,489 B2 | 6/2004 | Dua et al. |
| 6,015,378 | A | 1/2000 | Borst et al. | 6,754,536 B2 | 6/2004 | Swoyer et al. |
| 6,030,364 | A | 2/2000 | Durgin et al. | 6,755,849 B1 | 6/2004 | Gowda et al. |
| 6,030,392 | A | 2/2000 | Dakov | 6,755,869 B2 | 6/2004 | Geitz |
| 6,042,538 | A | 3/2000 | Puskas | 6,756,364 B2 | 6/2004 | Barbier et al. |
| 6,044,847 | A | 4/2000 | Carter et al. | 6,764,518 B2 | 7/2004 | Godin |
| 6,067,991 | A | 5/2000 | Forsell | 6,773,440 B2 * | 8/2004 | Gannoe et al. ............ 606/142 |
| 6,074,343 | A | 6/2000 | Nathanson et al. | 6,773,441 B1 | 8/2004 | Laufer et al. |
| 6,083,241 | A | 7/2000 | Longo et al. | 6,786,898 B2 | 9/2004 | Guenst |
| 6,086,600 | A | 7/2000 | Kortenbach | 6,790,214 B2 | 9/2004 | Kraemer et al. |
| 6,113,609 | A | 9/2000 | Adams | 6,802,868 B2 | 10/2004 | Silverman et al. |
| 6,119,913 | A | 9/2000 | Adams et al. | 6,821,285 B2 | 11/2004 | Laufer et al. |
| 6,120,513 | A | 9/2000 | Bailey et al. | 6,835,199 B2 | 12/2004 | McGuckin, Jr. et al. |
| 6,136,006 | A | 10/2000 | Johnson et al. | 6,835,200 B2 | 12/2004 | Laufer et al. |
| 6,159,146 | A | 12/2000 | El Gazayerli | 6,837,848 B2 | 1/2005 | Bonner et al. |
| 6,159,195 | A | 12/2000 | Ha et al. | 6,840,423 B2 | 1/2005 | Adams et al. |
| 6,165,183 | A | 12/2000 | Kuehn et al. | 6,845,776 B2 * | 1/2005 | Stack et al. ................. 128/898 |
| 6,179,195 | B1 | 1/2001 | Adams et al. | 6,896,682 B1 | 5/2005 | McClellan et al. |
| 6,186,942 | B1 | 2/2001 | Sullivan et al. | 6,926,722 B2 | 8/2005 | Geitz |
| 6,186,985 | B1 | 2/2001 | Snow | 6,966,919 B2 | 11/2005 | Sixto, Jr. et al. |
| 6,197,022 | B1 | 3/2001 | Baker | 6,981,978 B2 | 1/2006 | Gannoe |
| 6,200,318 | B1 | 3/2001 | Har-Shai et al. | 6,991,643 B2 | 1/2006 | Saadat |
| 6,206,822 | B1 | 3/2001 | Foley et al. | 7,020,531 B1 | 3/2006 | Colliou et al. |
| 6,206,893 | B1 | 3/2001 | Klein et al. | 7,025,791 B2 | 4/2006 | Levine et al. |
| 6,224,614 | B1 | 5/2001 | Yoon | 7,033,378 B2 | 4/2006 | Smith et al. |
| 6,231,561 | B1 | 5/2001 | Frazier et al. | 7,037,343 B2 | 5/2006 | Imran |
| 6,248,058 | B1 | 6/2001 | Silverman et al. | 7,037,344 B2 | 5/2006 | Kagan et al. |
| 6,254,642 | B1 | 7/2001 | Taylor | 7,063,715 B2 | 6/2006 | Onuki et al. |
| 6,273,897 | B1 | 8/2001 | Dalessandro et al. | 7,083,630 B2 | 8/2006 | DeVries et al. |
| 6,279,809 | B1 | 8/2001 | Nicolo | 7,087,011 B2 | 8/2006 | Cabiri et al. |
| 6,290,674 | B1 | 9/2001 | Roue et al. | 7,097,650 B2 | 8/2006 | Weller et al. |
| 6,293,923 | B1 | 9/2001 | Yachia et al. | 7,520,884 B2 * | 4/2009 | Swanstrom et al. ......... 606/153 |
| 6,302,917 | B1 | 10/2001 | Dua et al. | 2001/0014800 A1 | 8/2001 | Frazier et al. |
| 6,312,437 | B1 | 11/2001 | Kortenbach | 2001/0020190 A1 | 9/2001 | Taylor |
| 6,328,689 | B1 | 12/2001 | Gonzalez et al. | 2001/0037127 A1 | 11/2001 | De Hoyos Garza |
| 6,338,345 | B1 | 1/2002 | Johnson et al. | 2002/0022851 A1 | 2/2002 | Kalloo et al. |
| 6,352,543 | B1 | 3/2002 | Cole | 2002/0035361 A1 | 3/2002 | Houser et al. |
| 6,358,197 | B1 | 3/2002 | Silverman et al. | 2002/0040226 A1 | 4/2002 | Laufer et al. |
| 6,379,366 | B1 | 4/2002 | Fleischman et al. | 2002/0047036 A1 | 4/2002 | Sullivan et al. |
| 6,387,104 | B1 | 5/2002 | Pugsley, Jr. et al. | 2002/0058967 A1 | 5/2002 | Jervis |
| 6,398,795 | B1 | 6/2002 | McAlister et al. | 2002/0072761 A1 | 6/2002 | Abrams et al. |
| 6,416,535 | B1 | 7/2002 | Lazarus | 2002/0077661 A1 | 6/2002 | Saadat |
| 6,423,087 | B1 | 7/2002 | Sawada | 2002/0078967 A1 | 6/2002 | Sixto, Jr. et al. |
| 6,432,040 | B1 | 8/2002 | Meah | 2002/0082621 A1 | 6/2002 | Schurr et al. |
| 6,447,533 | B1 | 9/2002 | Adams | 2002/0143346 A1 | 10/2002 | McGuckin, Jr. et al. |
| 6,460,543 | B1 | 10/2002 | Forsell | 2002/0165589 A1 | 11/2002 | Imran et al. |
| 6,475,136 | B1 | 11/2002 | Forsell | 2002/0183768 A1 | 12/2002 | Deem et al. |
| 6,491,707 | B2 | 12/2002 | Makower et al. | 2002/0193816 A1 | 12/2002 | Laufer et al. |
| 6,494,888 | B1 | 12/2002 | Laufer et al. | 2003/0040804 A1 | 2/2003 | Stack et al. |
| 6,506,196 | B1 | 1/2003 | Laufer | 2003/0040808 A1 | 2/2003 | Stack et al. |
| 6,535,764 | B2 | 3/2003 | Imran et al. | 2003/0065340 A1 | 4/2003 | Geitz |
| 6,540,789 | B1 | 4/2003 | Silverman et al. | 2003/0065359 A1 | 4/2003 | Weller et al. |
| 6,551,310 | B1 | 4/2003 | Ganz et al. | 2003/0093117 A1 | 5/2003 | Saadat |
| 6,554,844 | B2 | 4/2003 | Lee et al. | 2003/0109892 A1 | 6/2003 | Deem et al. |

| | | |
|---|---|---|
| 2003/0109931 A1 | 6/2003 | Geitz |
| 2003/0109935 A1 | 6/2003 | Geitz |
| 2003/0120265 A1 | 6/2003 | Deem et al. |
| 2003/0120285 A1 | 6/2003 | Kortenbach |
| 2003/0120289 A1 | 6/2003 | McGuckin, Jr. et al. |
| 2003/0132267 A1 | 7/2003 | Adams et al. |
| 2003/0158563 A1 | 8/2003 | McClellan et al. |
| 2003/0158601 A1 | 8/2003 | Silverman et al. |
| 2003/0171760 A1 | 9/2003 | Gambale |
| 2003/0208209 A1 | 11/2003 | Gambale et al. |
| 2003/0225312 A1 | 12/2003 | Suzuki et al. |
| 2004/0006351 A1 | 1/2004 | Gannoe et al. |
| 2004/0009224 A1 | 1/2004 | Miller |
| 2004/0010271 A1 | 1/2004 | Kortenbach |
| 2004/0024386 A1 | 2/2004 | Deem et al. |
| 2004/0030347 A1* | 2/2004 | Gannoe et al. ............... 606/153 |
| 2004/0034371 A1* | 2/2004 | Lehman et al. ............... 606/144 |
| 2004/0037865 A1 | 2/2004 | Miller |
| 2004/0039452 A1 | 2/2004 | Bessler |
| 2004/0049209 A1 | 3/2004 | Benchetrit |
| 2004/0059349 A1 | 3/2004 | Sixto, Jr. et al. |
| 2004/0059354 A1 | 3/2004 | Smith et al. |
| 2004/0059358 A1 | 3/2004 | Kortenbach et al. |
| 2004/0082963 A1 | 4/2004 | Gannoe et al. |
| 2004/0087977 A1 | 5/2004 | Nolan et al. |
| 2004/0089313 A1 | 5/2004 | Utley et al. |
| 2004/0092892 A1 | 5/2004 | Kagan et al. |
| 2004/0092974 A1* | 5/2004 | Gannoe et al. ............... 606/153 |
| 2004/0097989 A1 | 5/2004 | Trigueros |
| 2004/0107004 A1 | 6/2004 | Levine et al. |
| 2004/0116949 A1 | 6/2004 | Ewers et al. |
| 2004/0122456 A1 | 6/2004 | Saadat et al. |
| 2004/0122473 A1 | 6/2004 | Ewers et al. |
| 2004/0122526 A1 | 6/2004 | Imran |
| 2004/0133147 A1 | 7/2004 | Woo |
| 2004/0133238 A1 | 7/2004 | Cerier |
| 2004/0138525 A1 | 7/2004 | Saadat |
| 2004/0138526 A1 | 7/2004 | Guenst |
| 2004/0138529 A1 | 7/2004 | Wiltshire et al. |
| 2004/0138531 A1 | 7/2004 | Bonner et al. |
| 2004/0138682 A1 | 7/2004 | Onuki et al. |
| 2004/0147958 A1 | 7/2004 | Lam et al. |
| 2004/0148021 A1 | 7/2004 | Cartledge et al. |
| 2004/0148034 A1* | 7/2004 | Kagan et al. ............... 623/23.65 |
| 2004/0158331 A1 | 8/2004 | Stack et al. |
| 2004/0162568 A1* | 8/2004 | Saadat et al. ............... 606/139 |
| 2004/0167546 A1 | 8/2004 | Saadat et al. |
| 2004/0172141 A1 | 9/2004 | Stack et al. |
| 2004/0181242 A1 | 9/2004 | Stack et al. |
| 2004/0193190 A1 | 9/2004 | Liddicoat et al. |
| 2004/0210243 A1 | 10/2004 | Gannoe et al. |
| 2004/0225183 A1 | 11/2004 | Michlitsch et al. |
| 2004/0225194 A1 | 11/2004 | Smith et al. |
| 2004/0225305 A1 | 11/2004 | Ewers et al. |
| 2005/0021681 A1 | 1/2005 | Oommen |
| 2005/0038415 A1 | 2/2005 | Rohr et al. |
| 2005/0049718 A1 | 3/2005 | Dann et al. |
| 2005/0055038 A1 | 3/2005 | Kelleher et al. |
| 2005/0055039 A1 | 3/2005 | Burnett et al. |
| 2005/0075622 A1 | 4/2005 | Levine et al. |
| 2005/0075653 A1 | 4/2005 | Saadat et al. |
| 2005/0080444 A1 | 4/2005 | Kraemer et al. |
| 2005/0085787 A1 | 4/2005 | Laufer |
| 2005/0096750 A1 | 5/2005 | Kagan et al. |
| 2005/0119671 A1 | 6/2005 | Reydel et al. |
| 2005/0143760 A1 | 6/2005 | Imran |
| 2005/0148818 A1 | 7/2005 | Mesallum |
| 2005/0149067 A1 | 7/2005 | Takemoto et al. |
| 2005/0149114 A1 | 7/2005 | Cartledge et al. |
| 2005/0194038 A1 | 9/2005 | Brabec et al. |
| 2005/0194294 A1 | 9/2005 | Oexle et al. |
| 2005/0194312 A1 | 9/2005 | Niemeyer et al. |
| 2005/0195925 A1 | 9/2005 | Traber |
| 2005/0195944 A1 | 9/2005 | Bartels et al. |
| 2005/0196356 A1 | 9/2005 | Leinen et al. |
| 2005/0197540 A1 | 9/2005 | Liedtke |
| 2005/0197622 A1 | 9/2005 | Blumenthal et al. |
| 2005/0197684 A1 | 9/2005 | Koch |
| 2005/0198476 A1 | 9/2005 | Gazsi et al. |
| 2005/0228415 A1 | 10/2005 | Gertner |
| 2005/0247320 A1* | 11/2005 | Stack et al. ............... 128/898 |
| 2005/0256587 A1 | 11/2005 | Egan |
| 2006/0020247 A1 | 1/2006 | Kagan et al. |
| 2006/0020254 A1 | 1/2006 | Hoffmann |
| 2006/0020276 A1 | 1/2006 | Saadat et al. |
| 2006/0036267 A1 | 2/2006 | Saadat et al. |

FOREIGN PATENT DOCUMENTS

| | | |
|---|---|---|
| EP | 0 174 843 A1 | 3/1986 |
| EP | 0 246 999 A1 | 11/1987 |
| EP | 0 540 010 A2 | 5/1993 |
| JP | 63277063 | 11/1988 |
| JP | 63279854 | 11/1988 |
| JP | 63302863 | 12/1988 |
| JP | 1049572 | 2/1989 |
| JP | 4297219 | 10/1992 |
| WO | WO 94/18893 A1 | 9/1994 |
| WO | WO 99/17662 A1 | 4/1999 |
| WO | WO 99/53827 A1 | 10/1999 |
| WO | WO 00/32137 A1 | 6/2000 |
| WO | WO 00/48656 A1 | 8/2000 |
| WO | WO 00/78227 A1 | 12/2000 |
| WO | WO 00/78229 A1 | 12/2000 |
| WO | WO 01/66018 A1 | 9/2001 |
| WO | WO 01/67964 A2 | 9/2001 |
| WO | WO 01/85034 A1 | 11/2001 |
| WO | WO 02/24080 A2 | 3/2002 |
| WO | WO 02/35980 A2 | 5/2002 |
| WO | WO 02/39880 A2 | 5/2002 |
| WO | WO 02/071951 A1 | 9/2002 |
| WO | WO 02/091961 A1 | 11/2002 |
| WO | WO 02/096327 A2 | 12/2002 |
| WO | WO 03/007796 A2 | 1/2003 |
| WO | WO 03/017882 A2 | 3/2003 |
| WO | WO 03/078721 A2 | 9/2003 |
| WO | WO 03/086247 A1 | 10/2003 |
| WO | WO 03/088844 A1 | 10/2003 |
| WO | WO 03/094785 A1 | 11/2003 |
| WO | WO 03/099140 A1 | 12/2003 |
| WO | WO 03/105563 A2 | 12/2003 |
| WO | WO 03/105671 A2 | 12/2003 |
| WO | WO 2004/009269 A2 | 1/2004 |
| WO | WO 2004/014237 A1 | 2/2004 |
| WO | WO 2004/017863 A2 | 3/2004 |
| WO | WO 2004/019787 A2 | 3/2004 |
| WO | WO 2004/019826 A1 | 3/2004 |
| WO | WO 2004/037064 A2 | 5/2004 |
| WO | WO 2004/049911 A2 | 6/2004 |
| WO | WO 2004/058102 A2 | 7/2004 |
| WO | WO 2004/060150 A1 | 7/2004 |
| WO | WO 2004/087014 A2 | 10/2004 |
| WO | WO 2004/103189 A1 | 12/2004 |
| WO | WO 2005/023118 A1 | 3/2005 |
| WO | WO 2005/037152 A1 | 4/2005 |
| WO | WO 2005/058239 A2 | 6/2005 |
| WO | WO 2005/060882 A1 | 7/2005 |
| WO | WO 2006/078781 A1 | 7/2006 |

OTHER PUBLICATIONS

Benjamin, S.B., *Small Bowel Obstruction and the Garren-Edwards Bubble, Lessons to be Learned?* Abstracts Submitted to A/S/G/E 1987, Division of Gastroenterology, Department of Medicine, Georgetown University Hospital, Washington, D.C.

Boyle, Thomas M., M.D., et al., Small Intestinal Obstruction Secondary to Obturation by a Garren Gastric Bubble, *The American Journal of Gastroenterology*, vol. 82, No. 1, pp. 51-53, 1987.

Cass. O.W., et al., *Long-Term Follow-Up of Patients With Percutaneous Endoscopic Gastrostomy (PEG)*, Abstracts Submitted to A/S/G/E 1987, Department of Medicine, Hennepin County Medical Center, Minneapolis, MN 55415.

Clark, Charlene, R.N., The Gastric Bubble: Medicine, Magic or Mania? *SGA Journal*, vol. 9, No. 2, pp. 45-47, Fall 1986.

Cummings, David E., M.D., et al., Plasma Ghrelin Levels After Diet-Induced Weight Loss or Gastric Bypass Surgery, *New England Journal of Medicine*, vol. 346, No. 21, pp. 1623-1630, May 23, 2002.

Davenport, Horace W., Ph.D., D.Sc., *Physiology of the Digestive Tract; An Introductory Text*, 3d Ed., Cover and Table of Contents.

DeMeester, Tom T., M.D., Evolving Concepts of Reflux: The Ups and Downs of the LES, *Canadian Journal of Gastroenterology*, vol. 16, No. 5, pp. 327-331, 2002.

De Waele, B., M.D., et al., Intragastric Balloons for Preoperative Weight Reduction, *Obesity Surgery*, vol. 10, pp. 58-60, 2000.

Edell, Steven L., et al., Radiographic Evaluation of the Garren Gastric Bubble, *American Journal of Radiology*, vol. 145, pp. 49-50, Jul. 1985.

Gray, Henry, R.R.S., Anatomy of the Human Body, *The Digestive System*, Thirtieth American Edition, pp. 1466-1467 (Undated).

Kirby, Donald F., Incomplete Small Bowel Obstruction by the Garren-Edwards Gastric Bubble Necessitating surgical Intervention, *The American Journal of Gastroenterology*, vol. 82, No. 3, pp. 251-253, 1987.

Nieben, Ole Gyring, et al., Intragastric Balloon as an Artificial Bezoar for Treatment of Obesity, *The Lancet*, pp. 198-199, Jan. 23, 1982.

Percival, Walter L., M.D., "The Balloon Diet": A Noninvasive Treatment for Morbid Obesity. Preliminary Report of 1908 Patients, *The Canadian Journal of Surgery*, vol. 27, No. 2, pp. 135-136.

Stoltenberg, P.H., et al., *Intragastric Balloon Therapy of Obesity: A Randomized Double-Blind Trial*, Abstracts of Papers 1985, Scott & White Clinic, Texas A&M College of Medicine, Temple, Texas.

Taylor, T. Vincent, et al., Gastric Balloons for Obesity, *The Lancet*, Abstract, Mar. 27, 1982.

Vandenplas, Y., et al., Intragastric Balloons in Adolescents With Morbid Obesity, *European Journal of Gastroenterology & Hepatology*, vol. 11, No. 3, pp. 243-245, 1999.

Villar, Hugo V., M.D., et al., Mechanisms of Satiety and Gastric Emptying After Gastric Partitioning and Bypass, *Surgery*, pp. 229-236, Aug. 1981.

Wullstein, C., et al., Compression Anastomosis (AKA-2) in Colorectal Surgery: Results in 442 Consecutive Patients, *British Journal of Surgery 2000*, pp. 1071-1075.

U.S. Appl. No. 10/773,883, filed Feb. 5, 2004 unpublished; Inventors: Gerbi et al.

U.S. Appl. No. 10/797,439, filed Mar. 9, 2004 unpublished; Inventors: Weller et al.

Büchler, M.W., M.D. et al., A Technique For Gastroplasty As A Substitute For The Esophagus: Fundus Rotation Gastroplasty, *Journal Of The American College Of Surgeons*, vol. 182, pp. 241-245, Mar. 1996.

Chang, Craig G. M.D. [1], et al.. Gastro-Clip® Gastroplasty: A Very Long-Term Complication, *Obesity Surgery*, 14, © FD-Communications Inc.. 2004.

Endo Gia Universal, Single UseStapler and Endo GIA Roticulator, Brochure, 8 pages, Undated.

Filipi, Charles J. M.D., et al., Transoral, Flexible Endoscopic Suturing For Treatment Of GERD: A Multicenter Trial, *Gastrointestinal Endoscopy*,. vol. 53, No. 4, pp. 416-422, 2001.

Guidant, Internet, AXIUS™ VACUUM 2 Stabilizer Systems, Internet Website—www.guidant.com/products/axius_vacuum.shtml, 8 pages, visited May 27, 2003.

Gukovsky-Reicher, S., M.D. et al., *Expandable Metal Esophageal Stents: Efficacy and Safety. Review of Current Literature Data and of 53 Stents Placed at Harbor-UCLA Medical Center*, www.medscape.com/viewarticle/423508_print pp. 1-20, Medscape General Medicine 4(1), 2003 © 2002 Medscape, downloaded Oct. 9, 2006.

Hepworth, Clive C. Frcs et al., Mechanical Endoscopic Methods Of Haemostasis For Bleeding Peptic Ulcers: A Review, *Bailliere's Clinical Gastroenterology*, vol. 14, No. 3 pp. 467-476, 2000.

Ikeda, Y. et al., New Suturing Device For Transanal Endoscopic Microsurgery, *Blackwell Science Ltd.* p. 1290, 1997.

Johnson & Johnson Gateway$^{SM}$ Endopath 3mm, 5mm and 10 mm Diameter Endoscopic Instruments, Internet Website—www.inigateway.com/home.ihtml?loc=USENG&page=viewContent&parentId-0900..., 3 pages, visited May 29, 2003.

Power Medical Interventions Digital and Wireless Medical Technology, Product Innovation: SurgASSIST™, Internet Website—www/pmi2.com/access_flexibility.asp, 6 pages, visited May 29, 2003.

Snowden Pencer, Diamon-Flex Angled Snake Retractor (class 1, 878.4800), Appendix F.f, Undated.

Swain, C. Paul, M.D. et al., An Endoscopic Sewing Machine, *Gastrointestinal Edoscopy*, vol. 32, No. 1 pp. 36-38 1986.

Swain, C. Paul, M.D., Endoscopic Sewing And Stapling Machines, *Endoscopy* pp. 205-210, © Georg Thieme Verlag Stuttgart, New York, 1997.

Swain, C. Paul, M.D. et al., An Endoscopic Stapling Device: The Development Of A New Flexible Endoscopically Controlled Device For Placing Multiple Transmural Staples In Gastrointestinal Tissue, *Gastrointestinal Endoscopy*, vol. 35, No. 4, pp. 338-339, 1989.

Swain, C, Paul, M,D., Endoseopic Suturing, *Bailliere's Clinical Gastroenterology*, Bailliere's Tindall,, vol. 13 No. 1, pp. 97-108, 1999.

* cited by examiner

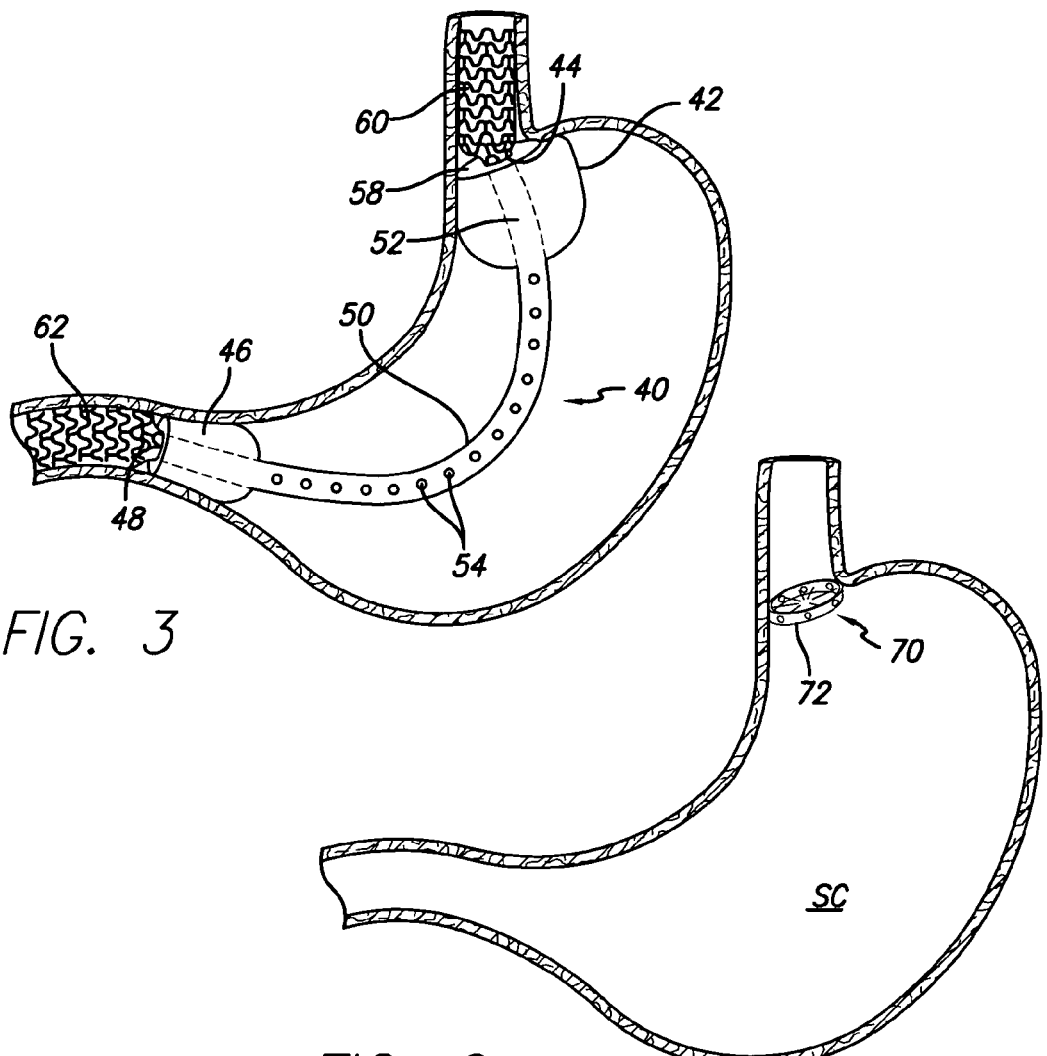
FIG. 3
FIG. 6
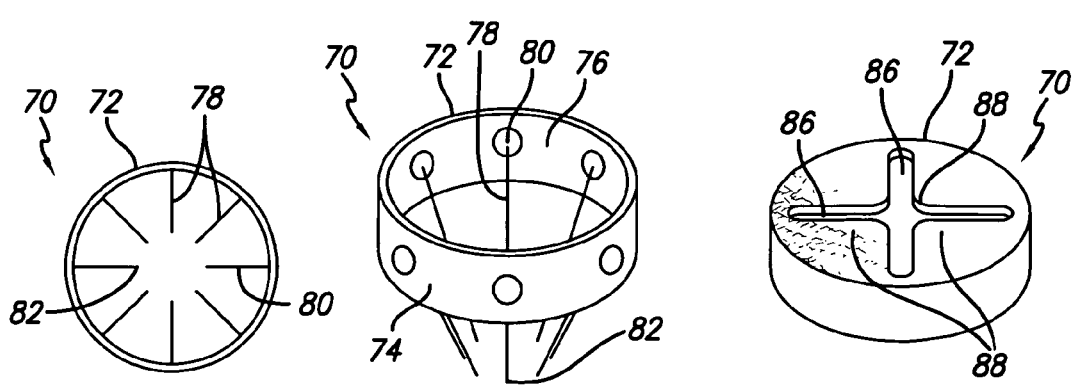
FIG. 4
FIG. 5
FIG. 7

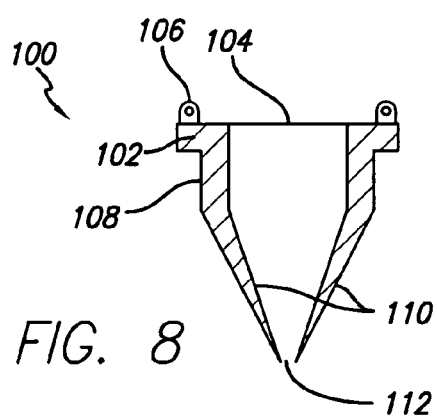
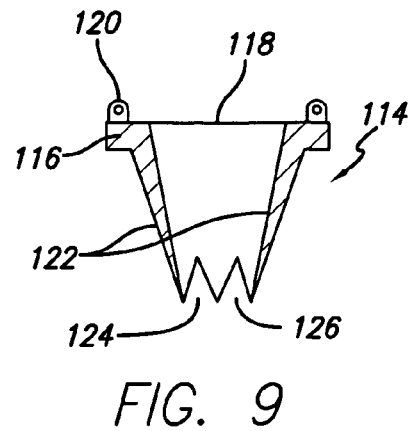
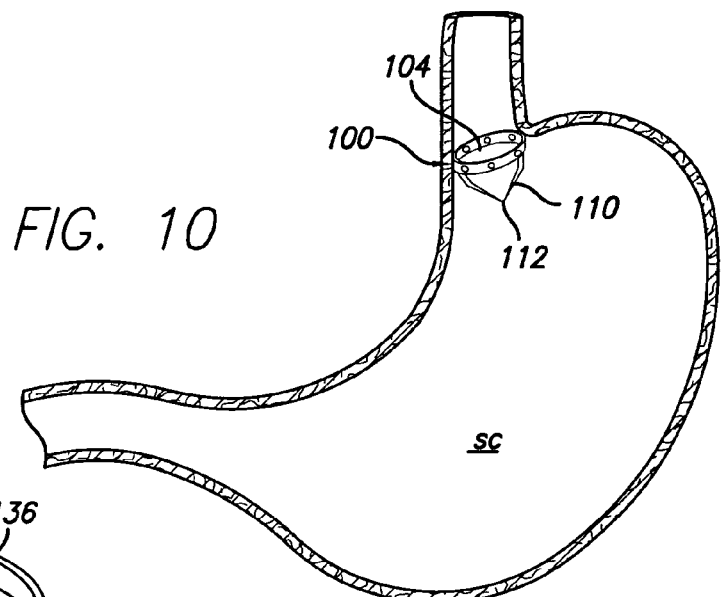
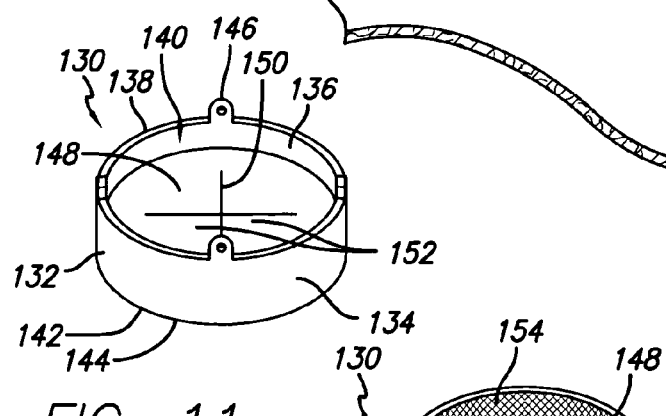
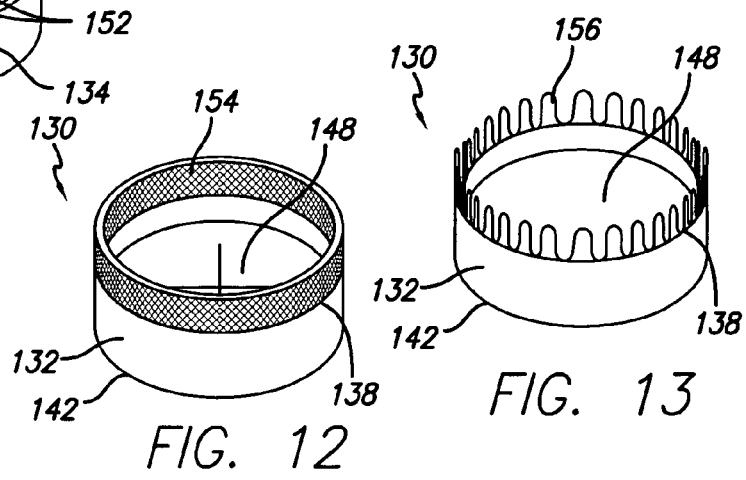
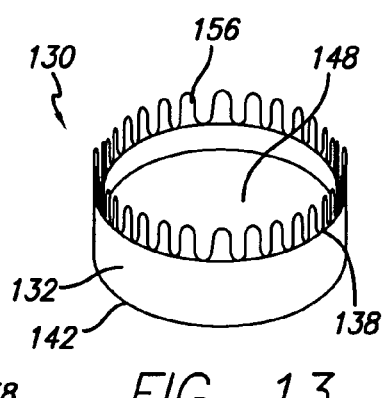

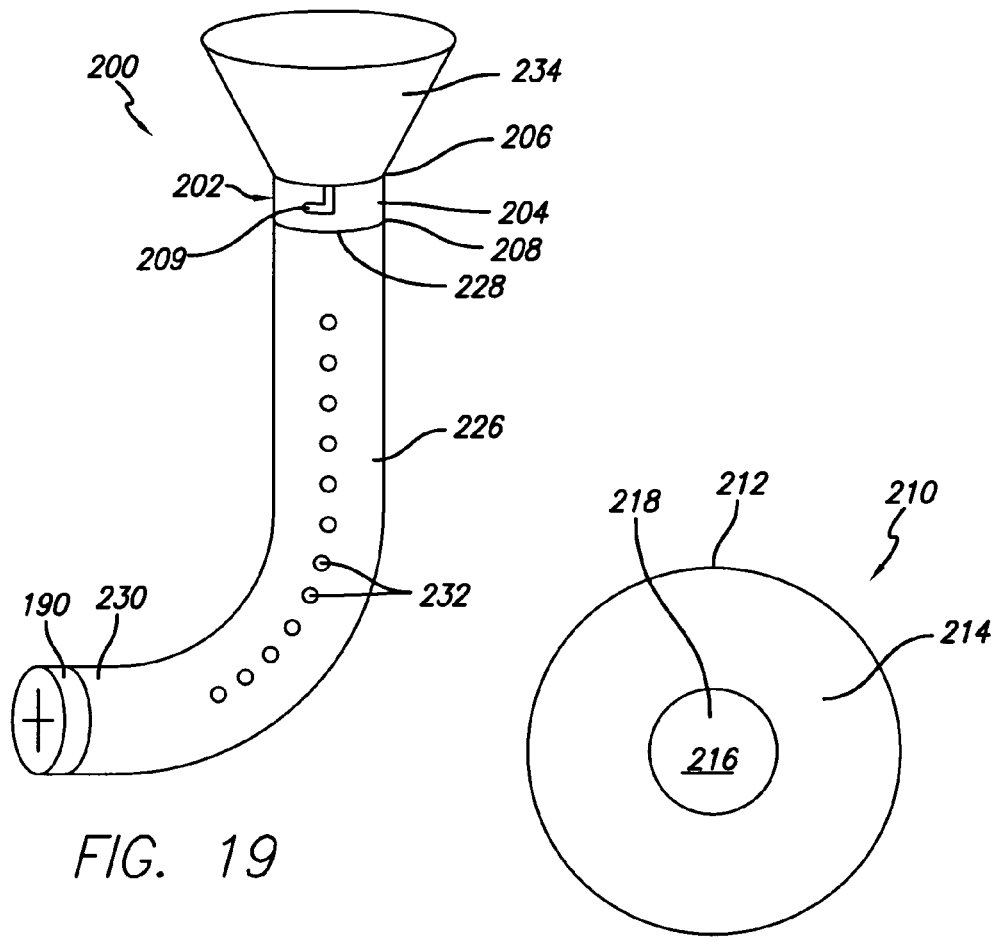
FIG. 19
FIG. 21
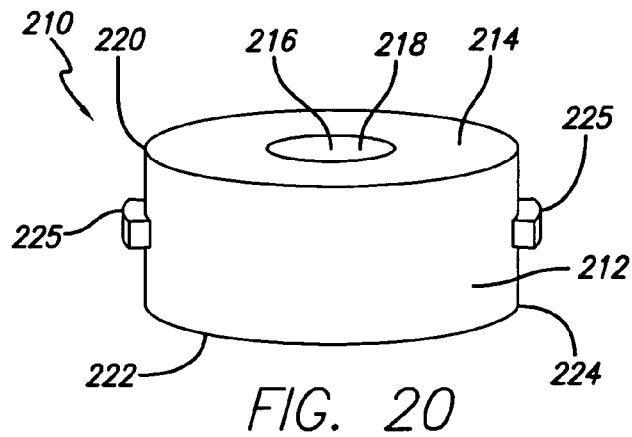
FIG. 20

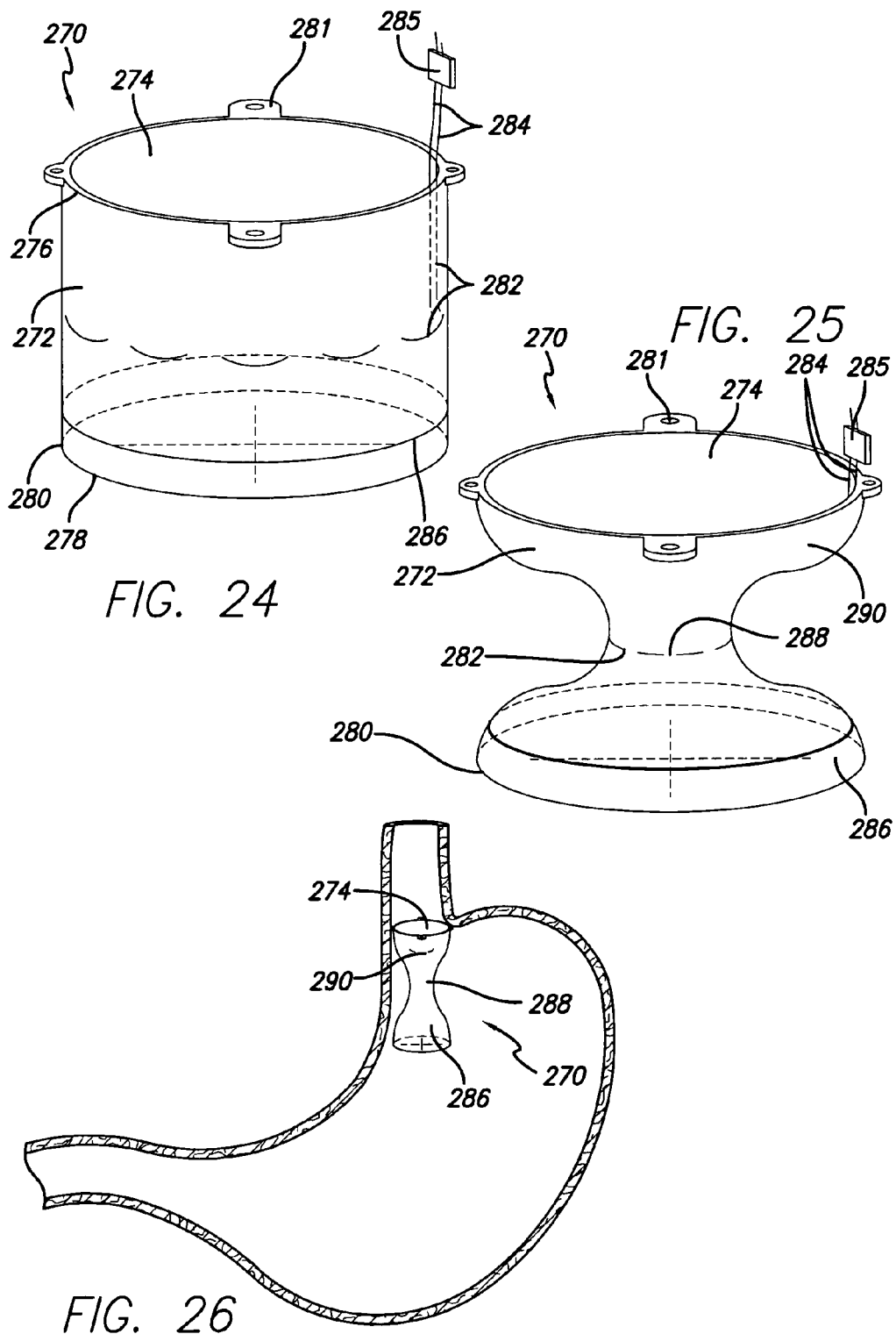

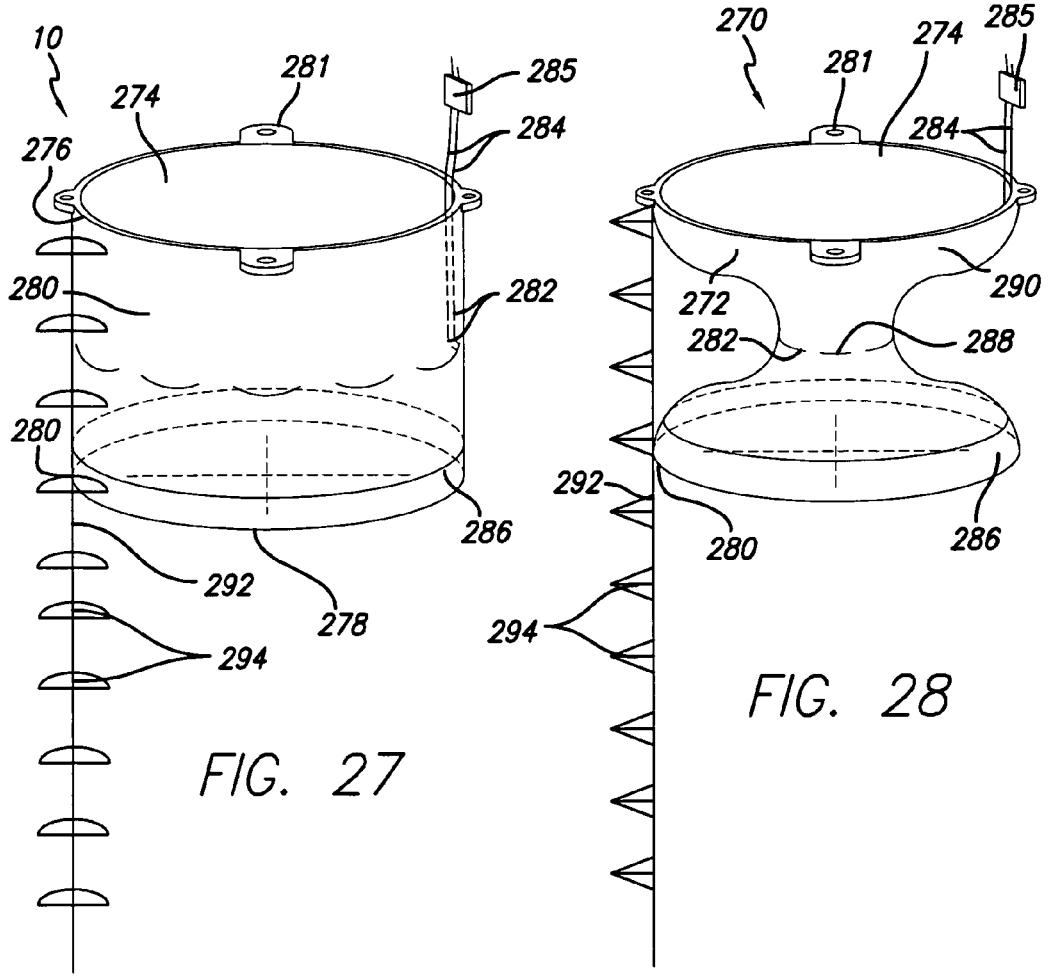
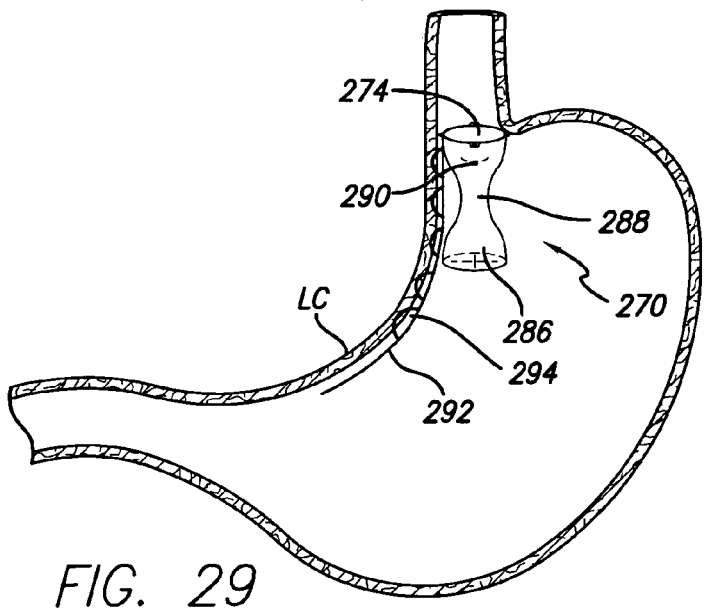

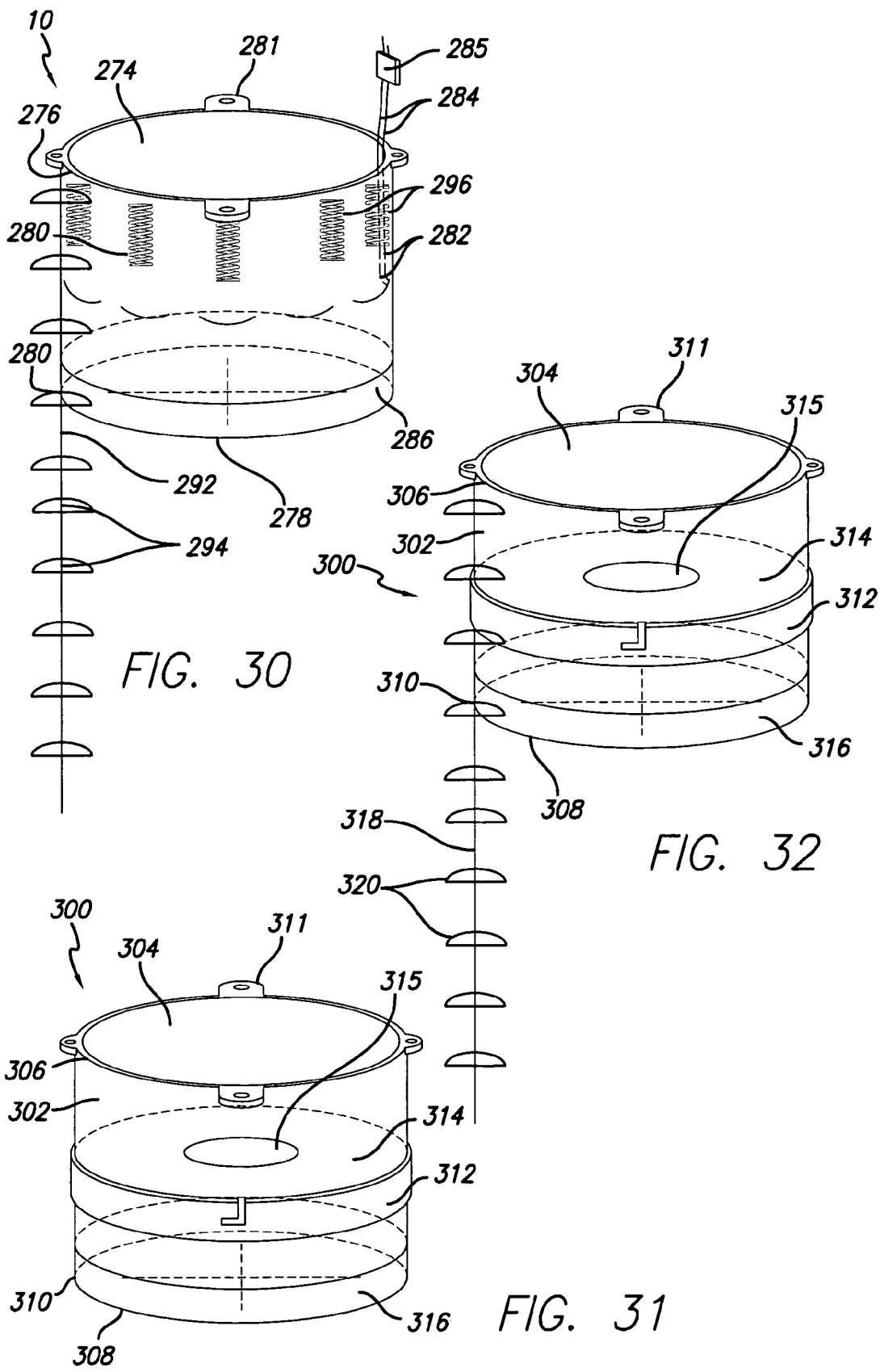

SYSTEMS AND METHODS FOR TREATING OBESITY

CROSS-REFERENCE TO RELATED APPLICATION

This application is claiming priority to the following provisional applications: U.S. Ser. No. 60/556,489 filed Mar. 26, 2004; and U.S. Ser. No. 60/569,037 filed May 10, 2004, the entire contents of each are incorporated herein by reference.

BACKGROUND OF THE INVENTION

1. Field of the Invention

The present invention pertains to medical equipment and more particularly to mechanical methods for reducing the volume of the stomach for the treatment of obesity.

2. General Background and State of the Art

Approximately 64% of Americans are overweight and obesity is rapidly becoming an epidemic resulting in a multitude of co-morbidities (e.g. cardiovascular disease, diabetes, etc.) and enormous medical costs. Approximately $75 billion dollars are spent each year on weight-related diseases in the US alone.

Historically, methods of weight reduction have ranged from oral pharmacological means, a multitude of diets, and various exercise programs. These approaches have generally resulted in temporary weight loss, with no or limited long-term benefit.

In recent years, the concept of obesity being a disease has gained momentum. To that end, surgical treatments have been developed to provide a more permanent solution (e.g. stomach stapling, gastric bypass, and the like). However, these treatments are generally surgical in nature, which imply inherent risk and high cost to the patient.

Thus, it remains desirable to develop new alternatives to provide non-invasive or minimally-invasive solutions to obesity.

SUMMARY OF THE INVENTION

The standard gastric bypass procedure provides not only a restrictive element (i.e., a small pouch to reduce food intake) but also allows food to bypass the majority of the stomach. This feature may result in improved weight loss for several reasons. One reason may be that the food never enters the stomach and thus, the production of the hormone ghrelin (produced in the fundus of the stomach) is reduced. Ghrelin stimulates appetite and fat accumulation, and therefore, a reduction in production of ghrelin could contribute to improved weight loss.

The gastric bypass procedure also bypasses a portion of the small intestine, which may lead to some malabsorption of nutrients, contributing to improved weight loss. It has also been shown that slowed gastric emptying may provide additional weight loss. To that end, several methods for slowing gastric emptying are provided.

A method for reducing the volume of the stomach involves inflating a hollow balloon that extends from the upper portion of the stomach down to approximately the duodenum. The balloon may be inflated with air, saline, or compounds which act to stiffen the balloon. In order to maintain a central lumen for food passage, the internal lumen of the balloon may be constructed of a less-compliant material than the outer surface of the balloon which contacts the stomach wall. The outer surface balloon material is designed to expand to contact the stomach wall and seal against it, whereas, the internal portion of the balloon is designed to provide a lumen and sufficient column strength to not longitudinally compress to dislodge the device. The internal lumen of the balloon may also be reinforced with a super-elastic wire form to prevent lumen collapse.

An alternative construction would provide two independently inflated balloons, one of which would seal near the esophageal-stomach junction and one which would seal near the stomach-duodenum junction. The balloons would be mounted on an extrusion with independent inflation lumens and a relatively large central lumen to allow for food passage. The food passage lumen may be fenestrated to allow for gastric juices to enter the food channel. The extrusion is sufficiently stiff to prevent radial or longitudinal collapse and the balloons aid in sealing against the stomach wall and further prevent migration. In yet another embodiment, this device is constructed such that a member attached to the distal balloon moves independently from the member attached to the proximal balloon in a telescoping manner to allow for length adjustment.

The above-mentioned balloon configurations may also incorporate proximal and/or distal stents or stent-grafts, which act to further mitigate the risk of migration of the device.

Another method for reducing stomach volume involves placing a valve structure into the stomach. Various valve structures may be utilized and act to limit the flow of ingested food into the stomach, resulting in feelings of satiety more quickly. One configuration may be a band with spokes that point towards the center of the band, but are not connected. These spokes are sufficiently resilient to only flex open to allow large amounts of food to pass. As the patient eats, food builds up on the spokes, until the weight is great enough to deflect said spokes, allowing the food to pass more readily. The band is attached to the stomach via various means, including staples, rivets, suture, adhesive or the like. The device may be constructed out of various resilient materials, including shape-memory alloys, stainless steel, Elgiloy, various polymers, or composites. Additionally, an optional band of fabric or mesh may be incorporated into the device to aid in attachment. Yet alternatively, a stent may be incorporated into the device to hold the device in position without the need for mechanical fixation, but may also be reinforced with said mechanical means.

An alternative configuration involves a valve structure consisting of a ring connected to a fabric or mesh substrate. The substrate may be constructed from polyester, PTFE, or the like. It is slitted to create at least one flap, and the flap(s) are constrained by a super-elastic wire form, which is sufficiently resilient to limit the flow of ingested food into the stomach. The wire form may be constructed from super-elastic materials, stainless steel, Elgiloy, or the like. Optionally, the wire form is also connected to the ring to provide additional stiffness. The ring may be constructed from various metals or polymers and incorporates anchoring points for attaching the device to the stomach wall.

Another valve design involves placing a valve similar to a "duckbill" or "double duckbill" configuration. The valves are sufficiently resilient to only flex open to allow large amounts of food to pass. As the patient eats, food builds up in the valve until the weight is great enough to deflect the flaps of the valve, allowing the food to pass more readily. The valve is attached to the stomach via various means, including staples, rivets, suture, adhesive or the like. The device may be constructed out of various resilient materials, including silicone, chronoprene, C-Flex, urethane, polyester fabric/mesh with shape-memory alloys, stainless steel, Elgiloy, various polymers, or composites. Additionally, an optional band of fabric or mesh may be incorporated into the device to aid in attachment. Yet alternatively, a stent may be incorporated into the device to hold the device in position without the need for mechanical fixation, but may also be reinforced with said mechanical means.

Another valve embodiment involves placing a slitted diaphragm in the stomach. The diaphragm has at least one slit, and may be constructed of pliable materials such as silicone, chronoprene, C-Flex, urethane, or other such materials. The diaphragm is sufficiently resilient to only flex open to allow large amounts of food to pass. As the patient eats, food builds up on the diaphragm until the weight is great enough to deflect the flaps of the valve, allowing the food to pass more readily. The valve is attached to the stomach via various means, including staples, rivets, suture, adhesive or the like. The device may be constructed out of various resilient materials, including silicone, polyester fabric/mesh with shape-memory alloys, stainless steel, Elgiloy, various polymers, or composites. Additionally, an optional band of fabric or mesh may be incorporated into the device to aid in attachment. Yet alternatively, a stent may be incorporated into the device to hold the device in position without the need for mechanical fixation, but may also be reinforced with the mechanical means.

A method for isolating food from the fundus is to provide a tube which bypasses food through the stomach without allowing it to enter the stomach itself. The tube could be constructed from reinforced PTFE or polyester (PET) and may optionally be fenestrated to allow for gastric juices to enter the remainder of the digestive tract.

There are also mechanical methods for slowing gastric emptying. A variety of pressure relief valves can be imagined, which are placed in the antrum of the stomach before the pyloric valve. The valves are designed to hold more pressure than the pyloric valve and only open when a minimum pressure is applied. Types of valves include, but are not limited to the previously-described duck-bill, double duck-bill, slitted diaphragm, and the like. Another valve type includes the flapper valve. These valves may be used in conjunction with the other elements of the present invention, including a restrictive element near the gastro-intestinal junction and an isolation element, such at a tube extending from the restrictive element to the pressure relief valve.

Finally, one of the major drawbacks of purely restrictive procedures is that the restriction does not adequately restrict fluid intake or provide a solution for individuals who eat (i.e., graze) small portions throughout the day. To mitigate this limitation, a combination device consisting of both a restrictive element and an element similar to those described as pressure relief valves throughout, may provide a solution. The device would be placed near the gastro-intestinal junction, provide an adjustable restriction to food intake, and provide a means to prevent continuous fluid consumption (e.g., shakes) and continuous food intake.

In yet another embodiment, a liner may be attached within the stomach cavity near the gastroesophageal junction ("GEJ"). An inlet end of the liner will be secured to the stomach wall by stapling the liner within a single or dual fold of the stomach wall around the circumference of the inlet end. The liner will also be secured along the lesser curve of the stomach, by placing plications to secure the liner within single or dual folds. The liner may extend along the lesser curve to the pylorous, or any length in between the GEJ and the pylorous.

It can be appreciated that all of the elements described herein may be configured in a multitude of combinations to achieve desired weight loss.

BRIEF DESCRIPTION OF THE DRAWINGS

FIG. 3 depicts another embodiment of the balloon device shown in FIG. 2 including a first stent connected to the first balloon and a second stent connected to the second balloon.

FIG. 4 depicts a top planar view of a valve.

FIG. 5 depicts a perspective view of the valve in FIG. 4.

FIG. 6 depicts a schematic view of the valve shown in FIG. 4 positioned near the gastrointestinal junction.

FIG. 7 depicts a planar view of another embodiment of a valve.

FIG. 8 depicts a cross-sectional view of a duckbill valve.

FIG. 9 depicts a cross-sectional view of a double duckbill valve.

FIG. 10 depicts a schematic view of the duckbill valve of FIG. 8 positioned near the gastrointestinal junction.

FIG. 11 depicts a perspective view of a slitted diaphragm valve.

FIG. 12 depicts a perspective view of another embodiment of the slitted diaphragm valve of FIG. 11 including a fabric/mesh band.

FIG. 13 depicts a perspective view of another embodiment of the slitted diaphragm valve of FIG. 11 including a stent.

FIG. 19 depicts another embodiment of a gastric device.

FIG. 20 depicts a perspective view of a stoma device.

FIG. 21 depicts a top planar view of the stoma device shown in FIG. 20.

FIG. 24 depicts a perspective view of an adjustable gastric device.

FIG. 25 depicts a perspective view of the adjustable gastric device of FIG. 24 with a suture tensioned to form a reduced stoma.

FIG. 26 depicts a schematic view of the adjustable gastric device of FIG. 25 attached in the stomach cavity near the gastrointestinal junction.

FIG. 27 depicts a perspective view of another embodiment of an adjustable gastric system including a spine.

FIG. 28 depicts a perspective view of the adjustable gastric system of FIG. 27 with a suture tensioned to form a reduced stoma.

FIG. 29 depicts a schematic view of the adjustable gastric device of FIG. 28 attached in the stomach cavity near the gastrointestinal junction.

FIG. 30 depicts a perspective view of another embodiment of an adjustable gastric system including a spine and a spring element.

FIG. 31 depicts a perspective view of another embodiment of an adjustable gastric system including a docking station.

FIG. 32 depicts a perspective view of another embodiment of the adjustable gastric system of FIG. 31 including a spine for attachment to the lesser curve of the stomach cavity.

DETAILED DESCRIPTION OF THE PREFERRED EMBODIMENTS

Methods and devices discussed in detail below are used to optimize patient weight loss. One method for simulating a gastric bypass and reducing the volume of the stomach involves placing a liner within the stomach cavity. Also, methods and devices for slowing gastric emptying involve placing valves within the stomach cavity near the gastro-intestinal junction and/or the pylorus. The methods and devices described below may prevent a patient from drinking and eating large volumes at one time and from eating slowly all day.

Figure 1:
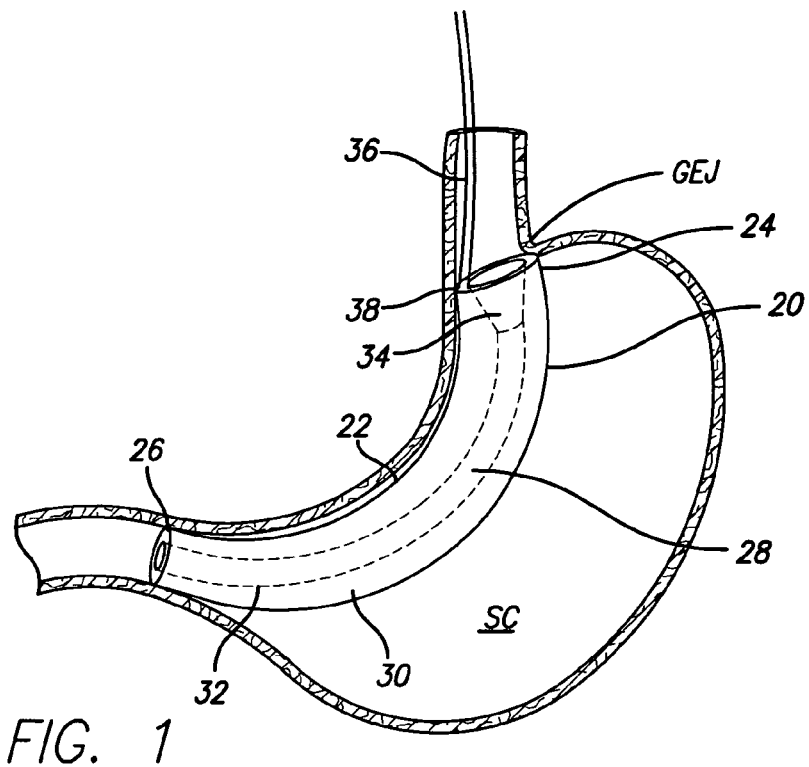
FIG. 1 depicts a schematic view of a hollow balloon liner inflated in the stomach cavity.

In one embodiment, a hollow balloon liner 20 is inflated and extended from the upper portion of the stomach, near the gastrointestinal junction down to approximately the duodenum. The inflated hollow balloon liner simulates a gastric bypass and reduces the volume of the stomach cavity. Referring to FIG. 1, the balloon includes a body 22 having a first or input end 24 and a second or output end 26, and a central lumen 28 extends between the first and second end of the balloon body. Also, the body of the balloon has an outer surface 30 and an inner surface 32 which defines the central lumen. In one embodiment, the length of the entire balloon body may be tapered from the first end to the second end. The first end of the balloon may have a larger diameter than the second end of the balloon, so that when inflated, the first end can secure itself near the gastrointestinal junction. At the second end, the diameter does not have to be as large as the first end to secure itself near the duodenum because of the size of the stomach anatomy. The central lumen may include a larger conical shape 34 near the first end of the balloon to help funnel food through the central lumen of the balloon. The remaining portion of the central lumen may have a consistent diameter, or in other embodiments the dimension of the central lumen may vary. In order to maintain a central lumen for food passage, the central lumen of the balloon may be constructed of a less-compliant material than the outer surface of the balloon which contacts the stomach wall. The outer surface balloon material is designed to expand to contact the stomach wall and seal against it, whereas, the internal portion of the balloon is designed to provide a lumen and sufficient column strength to not longitudinally compress to dislodge the device. The internal lumen of the balloon may also be reinforced with a super-elastic wire form to prevent lumen collapse. Balloon elements may be formed of compliant or noncompliant materials, such as thermoplastic elastomers and other materials including nylon, polyester, silicone, polyolefin, latex, cross-linked polyethylene, polyethylene terephthalate (PET), polyurethane and the like.

During the procedure for placing the balloon 20 within the stomach cavity, the balloon is deflated and advanced down the esophagus to the stomach cavity until the second end 26 is located near the duodenum and the first end 24 is positioned near the gastrointestinal junction. The balloon is next inflated using a fluid communication port or a catheter tube 36 that is also delivered down the esophagus and is removably connected to an inflation port 38 located on the body 22 of the balloon. The balloon may be filled with various materials to effect a temporary treatment (i.e., deflate and remove balloon) or a permanent treatment (i.e., a cross-linking material that hardens once balloon is inflated). Air, saline, or compounds which act to stiffen the balloon may be transported through the catheter tube and into the balloon. Once the balloon is inflated and secured against the stomach wall, the catheter is removed from the inflation port, leaving only the balloon which reduced the volume of the stomach.

Figure 2:
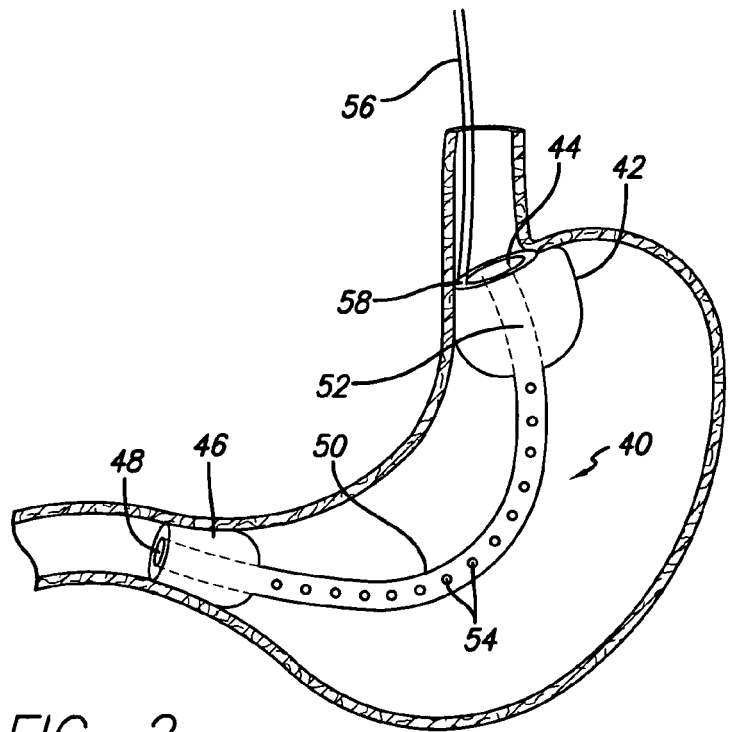
FIG. 2 depicts a schematic view of a balloon device having a tube connected between a first balloon inflated near the gastrointestinal junction and a second balloon inflated near the pylorus.

Another embodiment of a balloon device 40 is shown if FIG. 2. The balloon device includes a first balloon 42 located at a first or input end 44 and a second balloon 46 located at a second or output end 48. A cylindrical body or tube 50 is connected between the first and second balloons, and a central lumen 52 of the tube is in fluid communication with the first end and the second end to allow for food passage. In one embodiment, the balloons are mounted on the tube, so that the tube extends through the balloons. However, in another embodiment, the balloons are attached to the ends of the tube, so that each balloon forms an independent inflation lumen that is in communication with the central lumen of the tube. When inflated, the balloons aid in sealing against the stomach wall and further prevent migration of the balloon device. In yet another embodiment, this device is constructed such that a tubular member attached to the second or distal balloon moves independently from a tubular member attached to the first or proximal balloon in a telescoping manner to allow for length adjustment. The tube and the central lumen are sufficiently stiff to prevent radial or longitudinal collapse of the balloon device, the tube may optionally include fenestrations 54 to allow gastric juices to enter the new digestive tract which includes the central lumen of the balloon device. Similar to the above embodiment, the central lumen may include a larger conical shape near the first end of the balloon to help funnel food through the central lumen of the balloon device. The remaining portion of the central lumen may have a consistent diameter, or in other embodiments the dimension of the central lumen may vary. In order to maintain a central lumen for food passage, the cylindrical body or tube may include PET, Nylon, polyester, PTFE, polyethylene, polystyrene, polyurethane, polyethylene terephthalate. The material of the balloons is designed to expand to contact the stomach wall and seal against it, whereas, the tube of the balloon device is designed to provide a lumen and sufficient column strength to not longitudinally compress to dislodge the device. The central lumen of the tube may also be reinforced with a super-elastic wire to prevent the lumen from collapsing.

During the procedure for placing the balloon device 40 within the stomach cavity, the first and second balloons 42 and 44 are deflated and advanced down the esophagus, along with the tube 50, to the stomach cavity. The first balloon is positioned near the gastro-intestinal junction and the second balloon is positioned near the stomach-duodenum junction. The balloons are next inflated using a fluid communication port or a catheter tube 56 that is also delivered down the esophagus and is removably connected to an inflation port 58 located on the body of the first balloon. In one embodiment, only one inflation port is needed to inflate both the first and the second balloon, where an inflation lumen is disposed on the balloon device and in fluid communication between the first and second balloons. Yet in another embodiment, there may be separate inflations ports for independently inflating each balloon. The balloons may be filled with various materials to effect a temporary treatment (i.e., deflate and remove balloon) or a permanent treatment (i.e., a cross-linking material that hardens once balloon is inflated). Air, saline, or compounds which act to stiffen the balloons may be transported through the catheter tube and into the balloon. Once the balloons are inflated and secured against the stomach wall, the catheter is removed from the inflation port, leaving only the balloons which reduced the volume of the stomach.

Another embodiment of the balloon device 40 is shown in FIG. 3, where optional stents are included to improve fixation of the device and prevent migration within the stomach cavity. In this embodiment a first or proximal stent 60 is attached to the proximal end of the first balloon 42, and a second or distal stent 62 is attached to the distal end of the second balloon 46. The stents may be self expanding or balloon expandable, each of which are known in the art. In operation, the proximal stent 60 may be connected to the liner via a strut or narrowing, so that placement of the proximal stent in the esophagus does not impair the function of the lower esophageal sphincter (LES). By having a low profile strut of narrowing connecting the two, the force of the LES could overcome the structure and not be compromised (i.e. kept open), but the stent and the liner device could remain coupled for purposes of anchoring the prosthesis within the gastric cavity.

Another method for reducing stomach volume involves placing a valve structure into the stomach. As will be described in detail, various valve structures may be utilized and act to limit the flow of ingested food into the stomach, resulting in feelings of satiety more quickly. Referring to FIGS. 4 through 6, one embodiment of a valve 70 includes a band or circular body 72 having an outer surface 74 and an inner surface 76. The valve also include a plurality of restriction members or spokes 78 that each have an attached end 80 connected to the inner surface of the band and a free end 82 that points towards the center of the band. The free ends of the spokes are not connected together, and may or may not contact one another. In use, the resilient members or spokes are sufficiently resilient to only flex open to allow large amounts of food to pass. As the patient eats, food builds up on the spokes, until the weight is great enough to deflect the spokes, as shown in FIG. 5, allowing the food to pass more readily. As best shown in FIG. 4, the spokes are depicted in a wire-form configuration, but could be tubes, ribbon, cable, braid, or other geometry. Additionally, the spokes may be straight as shown, or they may have a shape set into them.

The valve 70 may be attached to the stomach wall via various means, including anchors, staples, rivets, suture, adhesive or the like, such as those disclose in U.S. Ser. Nos. 11/056,327 and 11/067,598, the entire contents of each are incorporated herein by reference. In one embodiment, an optional band of fabric or mesh may be incorporated into the valve device to aid in attachment, whereby the anchors or staples would be placed through the fabric or mesh bands and into the stomach wall. Yet in another embodiment, a stent may be incorporated into the valve device to hold the valve device in position without the need for mechanical fixation, but may also be reinforced with mechanical means. The valve may be anywhere along the length of the stomach cavity, however, it is preferred that the valve be positioned near the gastrointestinal junction, as shown in FIG. 6, so that the valve restricts incoming food. The band 72 and the spokes 78 of the valve may be constructed out of various resilient materials, including shape-memory alloys, stainless steel, Elgiloy, various polymers, or composites.

Another embodiment of the valve device 70 is shown in FIG. 7. Instead of spokes being connected to the inner surface of the band 72, a fabric or mesh substrate 84 is attached to the inner surface of the band or ring. The fabric/mesh substrate may be constructed from polyester, PTFE, or the like. In one embodiment, the fabric mesh substrate includes at least one slit 86 to create at least two flaps 88. FIG. 7 shows the fabric/mesh substrate to include two slits and four flaps. The flaps may be constrained by a wire form 90, which is sufficiently resilient to limit the flow of ingested food into the stomach. The wire form may be constructed from superelastic materials, such as nitinol, stainless steel, Elgiloy, or the like. Optionally, the wire form may be connected to the band or ring to provide additional stiffness. The band or ring may be constructed from various metals or polymers and incorporates anchoring points for attaching the device to the stomach wall.

Another valve embodiment is shown in FIGS. 8 through 10 and involves placing a valve similar to a "duckbill" or "double duckbill" configuration within the stomach cavity near the esophagus/stomach junction. The duckbill valve 100 includes an upper circular portion 102 that defines an inlet 104, and eyelets or attachment points 106 disposed on the upper circular portion for attaching the valve to the stomach wall. In one embodiment as shown in FIG. 8, the duckbill valve includes a central portion 108 that is cylindrical and a distal tapered portion or flaps 110 that taper downward to form an outlet 112 that is smaller in diameter than the inlet.

In another embodiment as shown in FIG. 9, a double duckbill valve 114 includes an upper circular portion 116 that defines an inlet 118, and eyelets or attachment points 120 disposed on the upper circular portion for attaching the valve to the stomach wall. In one embodiment, the double duckbill valve includes a distal tapered portion or flaps 122 that taper downward to form a first outlet 124 and a second outlet 126. The combined diameter of the first and second outlets is smaller than the diameter of the inlet. In another embodiment, the double duckbill valve may also include a central cylindrical portion disposed between the upper circular portion and the distal tapered portion.

The duckbill valve 100 or the double duckbill valve 114 is to be delivered to the stomach cavity and positioned near the gastrointestinal junction as shown in FIG. 10. Both of the valves 100 and 114 are sufficiently resilient to only flex open to allow large amounts of food to pass. As the patient eats, food builds up in the valve until the weight is great enough to deflect the flaps of the valve, allowing the food to pass more readily. The valve 100 or 114 is attached to the stomach via various means, including anchors, staples, rivets, suture, adhesive or the like that are secured through the eyelets 106 or 120 and into the stomach wall. The duckbill or double duckbill valve may be constructed out of various resilient materials, including silicone, chronoprene, C-Flex, urethane, polyester fabric/mesh with shape-memory alloys, stainless steel, Elgiloy, various polymers, or composites. Additionally, an optional band of fabric or mesh may be incorporated into the device to aid in attachment. Yet alternatively, a stent may be incorporated into the device to hold the device in position without the need for mechanical fixation, but may also be reinforced with the mechanical means.

Another valve embodiment is shown in FIGS. 11 through 13. FIG. 11 depicts slitted diaphragm valve 130 that includes a cylindrical body 132 having an outer surface 134 and an inner surface 136. The cylindrical body has a first end 138 defining an inlet 140 and a second end 142 defining an outlet 144. Eyelets or attachment points 146 are disposed at the first end of the cylindrical body and are used to help secure the valve to the stomach wall. A diaphragm 148 is attached to the inner surface of the cylindrical body and includes at least one slit 150 forming at least two flaps 152. As shown in FIG. 11, one embodiment includes a diaphragm with two slits forming four flaps. The diaphragm may be constructed of pliable materials such as silicone, chronoprene, C-Flex, urethane, or other such materials. Also, the diaphragm is sufficiently resilient to only flex open to allow large amounts of food to pass. As the patient eats, food builds up on the diaphragm until the weight is great enough to deflect the flaps of the valve, allowing the food to pass more readily. The valve is attached to the stomach near the gastrointestinal junction via various means, including anchors, staples, rivets, suture, adhesive or the like, that are secured through the eyelets and into the stomach wall. The cylindrical body may be constructed out of various resilient materials, including silicone, polyester fabric/mesh with shape-memory alloys, stainless steel, Elgiloy, various polymers, or composites.

In other embodiment as shown in FIG. 12, an optional band of fabric or mesh 154 may be disposed on the first end 138 of the cylindrical body 132 to aid in attachment. The fabric/mesh band may be constructed from polyester or the like. Once the valve 130 is positioned within the stomach, anchors, staples, rivets, sutures, or adhesives could then be positioned through the fabric/mesh band into the stomach wall to secure the valve.

In another embodiment as shown in FIG. 13, a stent 156 may be disposed on the first end 138 of the cylindrical body of the valve 130 to hold the valve in position without the need for mechanical fixation. The stent may be a self-expanding stent or a balloon-expandable stent, both or which are known in the art. Once the valve is positioned within the stomach cavity, the stent may be expanded provide a frictional fixation to the esophagus and/or upper portion of the stomach. In addition, other mechanical means, such as the use of anchors, staples, rivets, sutures, or adhesives, may also be used in conjunction with the stent to secure the valve. In another embodiment, the stent may also be covered in the fabric or mesh described in FIG. 12 to facilitate attachment to the stomach wall.

Figure 14:
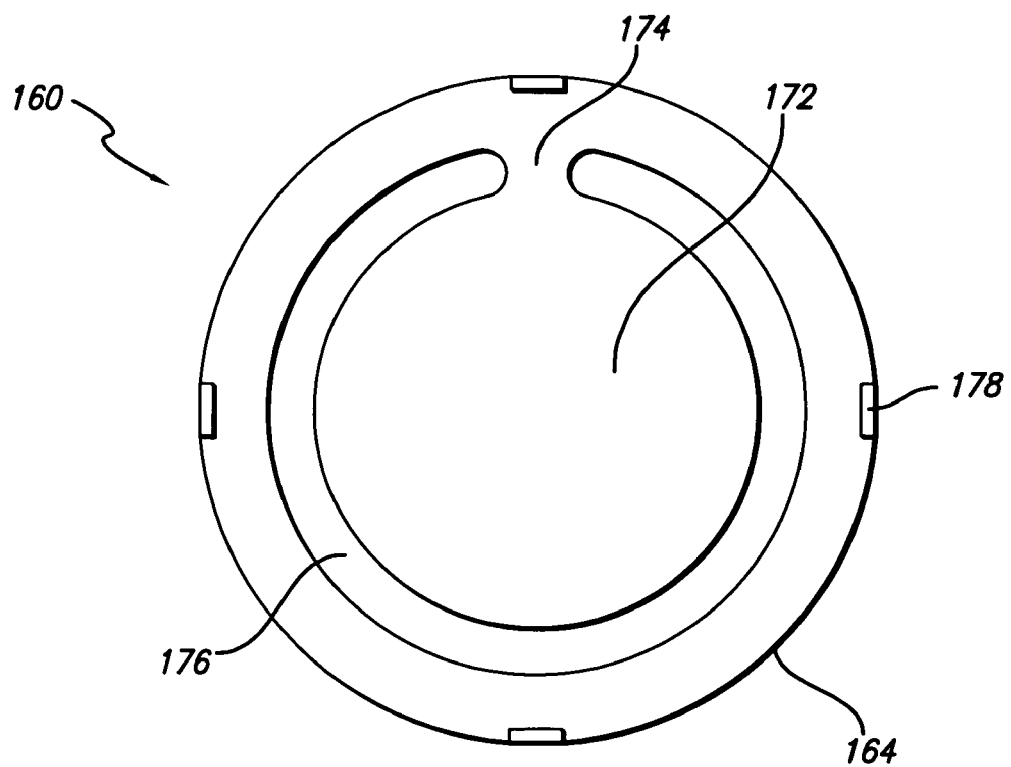
FIG. 14 depicts a top planar view of a flapper valve.
Figure 15:
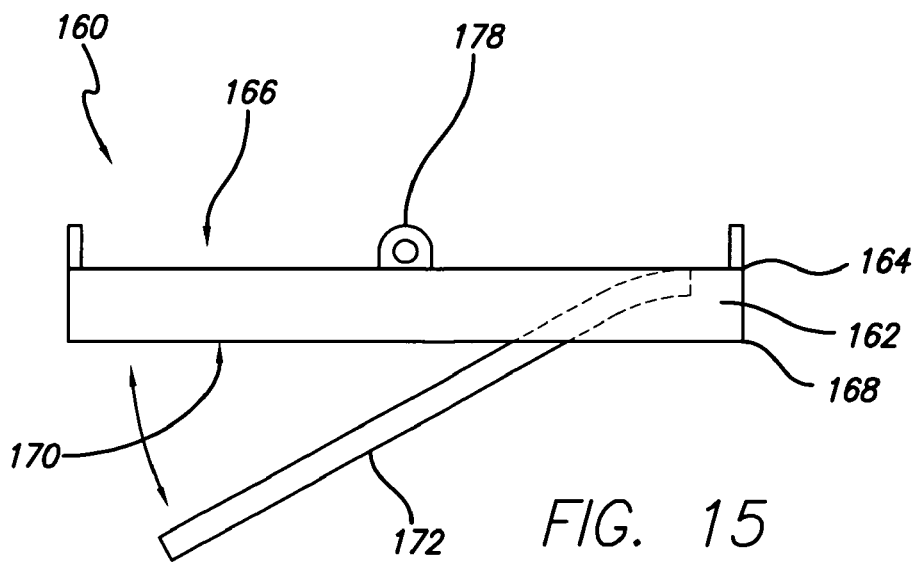
FIG. 15 depicts a side elevational view of the flapper valve shown in FIG. 14 in an open configuration.

Yet another embodiment of a valve is shown in FIGS. 14 and 15. A flapper valve 160 includes a cylindrical body 162 having a first end 164 defining a inlet 166 and a second end 168 defining an outlet 170. A flap 172 is disposed near the first end of the cylindrical body and attached at a connection point 174 to the cylindrical body, leaving a small gap or space 176 between the flap and the cylindrical body. Eyelets or attachment points 178 are disposed at the first end of the cylindrical body to aid in attaching the flapper valve to the stomach wall. In a closed configuration as shown in FIG. 14, the flap blocks the inlet of the valve. The connection between the flap and the cylindrical body is sufficiently resilient to only flex open to allow large amounts of food to pass. As the patient eats, food builds up on the flap until the weight is great enough to deflect the flap of the valve to an open configuration, as shown in FIG. 15, allowing the food to pass more readily. The flapper valve may be attached to the stomach near the gastrointestinal junction via various means, including anchors, staples, rivets, suture, adhesive or the like, that are secured through the eyelets and into the stomach wall. The cylindrical body and flap may be constructed out of various resilient materials, including silicone, polyester fabric/mesh with shape-memory alloys, stainless steel, Elgiloy, various polymers, or composites.

Figure 16:
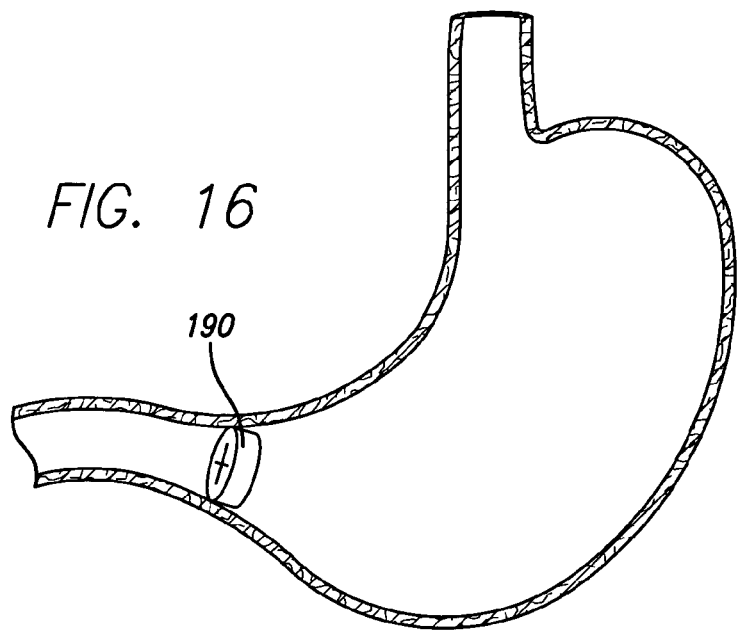
FIG. 16 depicts a schematic view of a pressure relief valve disposed near the pylorus.

In one embodiment of a method for slowing gastric emptying, a variety of pressure relief valves 190 can be placed in the antrum of the stomach before the pyloric valve as shown in FIG. 16. The pressure relief valve may be any of the valves previously discussed, including the valve 70, the duckbill or double duckbill valve 100 or 114, the slitted diaphragm valve 130, or the flapper valve 160. The pressure relief valve are designed to hold more pressure than the pyloric valve, and will only open when a minimum pressure is applied.

Figure 17:
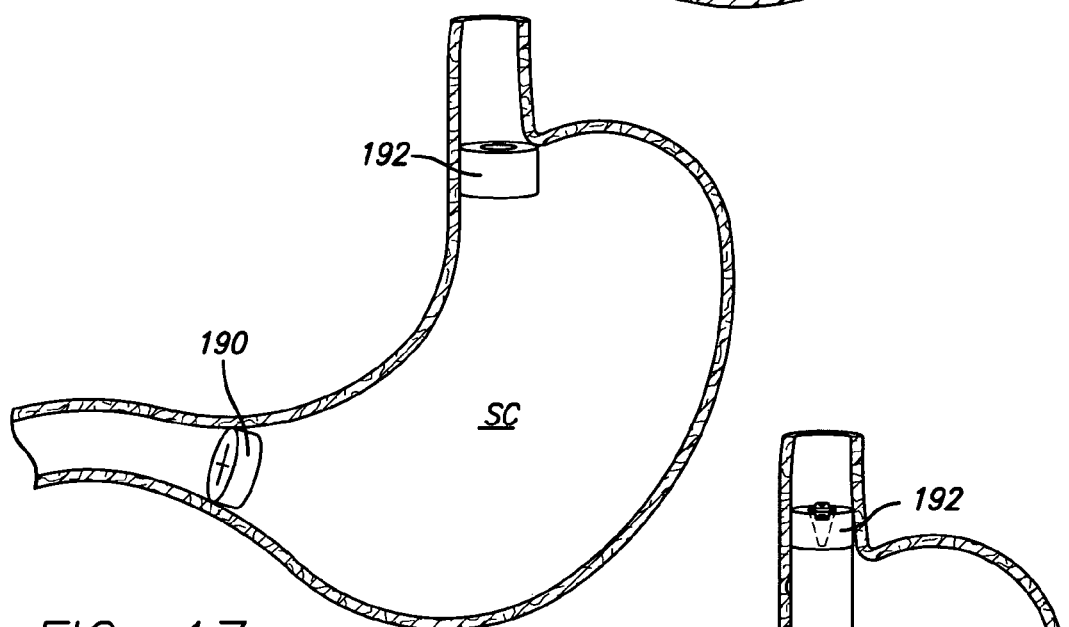
FIG. 17 depicts a schematic view of a pressure relief valve disposed near the pylorus and a restrictive valve disposed near the gastrointestinal junction.

In another embodiment of a method for slowing gastric emptying, the pressure relief valve 190 may be used in conjunction with a restrictive valve or device 192 placed near the gastro-intestinal junction as shown in FIG. 17. The restrictive valve or device 192 may be any of the valves previously discussed, including the valve 70, the duckbill or double duckbill valve 100 or 114, the slitted diaphragm valve 130, or the flapper valve 160. The pressure relief valve and the restrictive valve may be identical valves or they may be different valves depending on the embodiment. The restrictive valve builds food up at the valve until the weight is great enough to open the valve and allow food to pass more readily.

Figure 18:
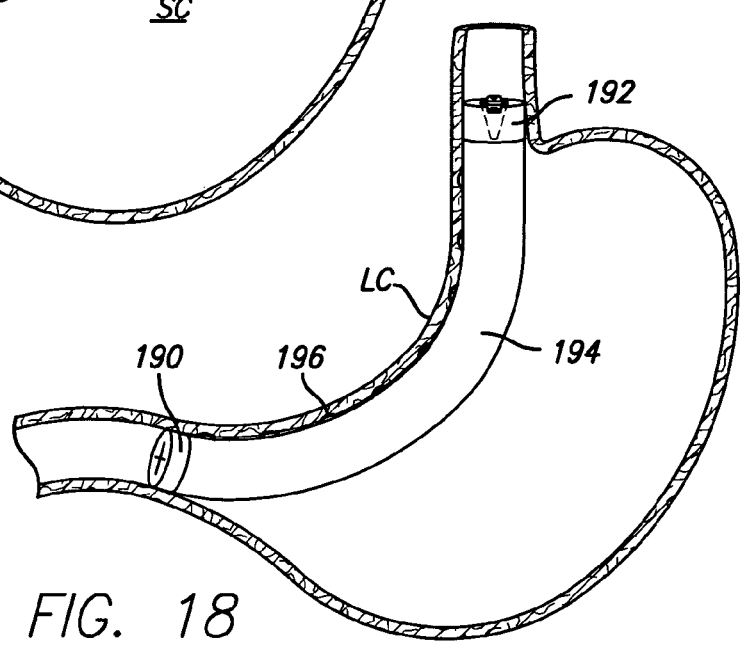
FIG. 18 depicts a schematic view of an isolation element or liner connected between the pressure relief valve and restrictive valve of FIG. 17.

In yet another embodiment of a method for slowing gastric emptying, an isolation element 194, such as a reinforced PTFE or PET graft, is connected between the pressure relief valve 190 and restrictive valve 192 as shown in FIG. 18. The isolation element includes a lumen that is in fluid communication with the outlet of the restrictive valve and the inlet of the pressure relief valve. In one embodiment the isolation element is attached to the lesser curve LC of the stomach with attachment devices 196, such as anchors, staples, rivets, sutures, adhesives, or the like. As a patient eats, food will travel through the restrictive valve and into the isolation element, where it will stay until enough pressure opens the pressure relief valve. It would be possible to place fenestrations within the isolation element to allow gastric juices to flow into the lumen of the isolation element.

Another embodiment of a method and device for slowing gastric emptying is shown in FIGS. 19 through 21. FIG. 19 is a schematic of a gastric device 200 which demonstrates the ability to adjust the stoma size for the restriction of food intake. The device includes a docking station 202, in which various stomas sized matingly engage. The docking station has a cylindrical body 204 with a first end 206 and a second end 208, and at least one slot 209 disposed along the cylindrical body. As shown in FIG. 19, the slot is L-shaped and extends through the first end of the cylindrical body. In one embodiment, there are two slots opposite each other on the cylindrical body. The cylindrical body of the docking station has a diameter that allows for a stoma device 210 to be docked within the docking station.

FIGS. 20 and 21 depict the stoma device having a donut shape. The stoma device includes a cylindrical body 212 having a wall 214 with a thickness that determines the size of a stoma or through hole 216 formed in the center of the cylindrical body. It is preferred that the diameter of the stoma 216 range between about 5 mm and about 20 mm, although the diameter of the stoma may be smaller than 5 mm and larger than 20 mm. An inlet 218 is defined at a first end 220 of the stoma device and an outlet 222 is defined at a second end 224 of the stoma device. In one embodiment, the stoma or through hole may be tapered from the inlet to the outlet to encourage food to travel downward. Also, tabs or lips 225 are formed opposite one another on the outer surface of the stoma device, which engage with the slots 206 of the docking station. In other embodiments, the stoma device may be secured to the docking station 202 with threads, magnetic force, clips, or other mechanical locking means. In use, a physician may easily replace one stoma device for another having a different sized stoma or through hole. For example, if the patient is not losing sufficient weight, a stoma device with a smaller stoma or through hole may be placed within the docking station. Conversely, if the patient is losing too much weight, or if the patient is vomiting excessively, a stoma device with a larger stoma or through hole may be placed within the docking station. It can be appreciated that this docking station may be compatible with many of the valve devices described above. Also, the stoma device may be the restrictive valve or device described in other embodiments above.

Referring again to FIG. 19, the gastric device 200 may also include a food tube or isolation element 226, such as a reinforced PTFE or PET graft, with a first end 228 and a second end 230. The first end is attached to the second end 208 of the docking station 202, and the second end may be connected to a pressure relief valve 190, which has already been described. In one embodiment, the gastric device does not include the pressure relief valve, and the second end is positioned to be in communication with the pylorus. Fenestrations 232 may be disposed along the food tube to allow gastric juices to enter a lumen of the food tube. In one embodiment the food tube or isolation element may be attached to the lesser curve LC of the stomach with attachment devices 196, such as anchors, staples, rivets, sutures, adhesives, or the like. Additionally a funnel 234 may be disposed on the first end 206 of the docking station to encourage food to flow downward to the stoma device 210.

Figure 22:
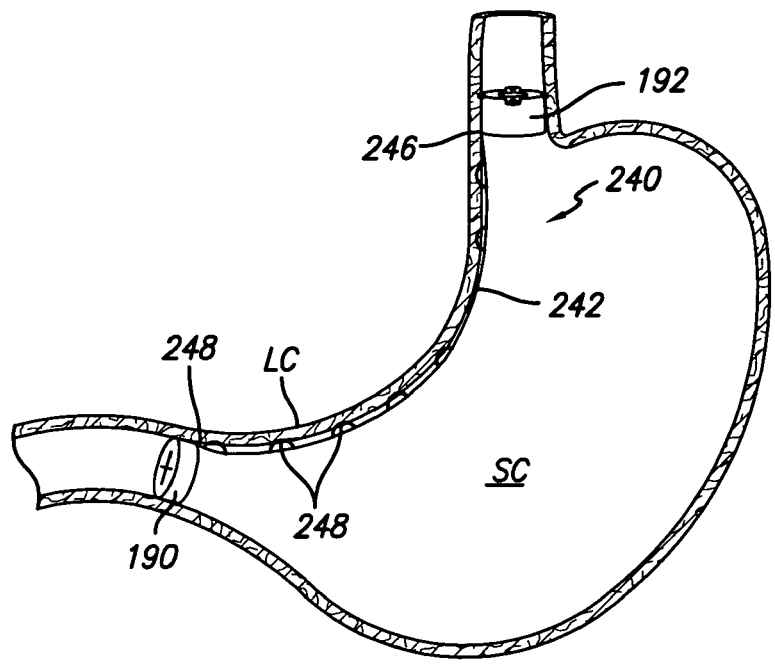
FIG. 22 depicts a schematic view of another embodiment of a gastric device attached to the lesser curve of the stomach cavity.

Another embodiment of a gastric device 240 and method for slowing gastric emptying is shown in FIG. 22. The device includes a pressure relief valve 190 and a restrictive valve 192, both of which have already been described. In this embodiment, a spine 242 has a first end 244 attached to the restrictive valve and a second end 246 attached to the pressure relief valve. The spine includes clips 248 attached along the length of the spine which may be crimped into the stomach wall during placement. The device 240 is situated within the stomach cavity so that the spine is secured along the lesser curve LC or the stomach. The spine provides column strength to the device, allowing for fewer attachment points near the gastro-intestinal junction. It also provides additional attachment points, which act to reduce the amount of stress on any one attachment point, thus leading to a more durable attachment. The pressure relief valve may be incorporated to slow gastric emptying, and in another embodiment may not be included in the gastric device. Alternatively, the spine may be attached to the lesser curve via clips, sutures, or the like, and not be pre-attached to the spine. Alternatively, the length of the spine may be adjustable to allow for various patient geometries. One method for adjusting the length of the spine is to employ a telescoping mechanism. Still in another embodiment, a fabric/mesh band may be attached to the spine, allowing for sutures or staples to more easily attach the spine to the lesser curve.

Figure 23:
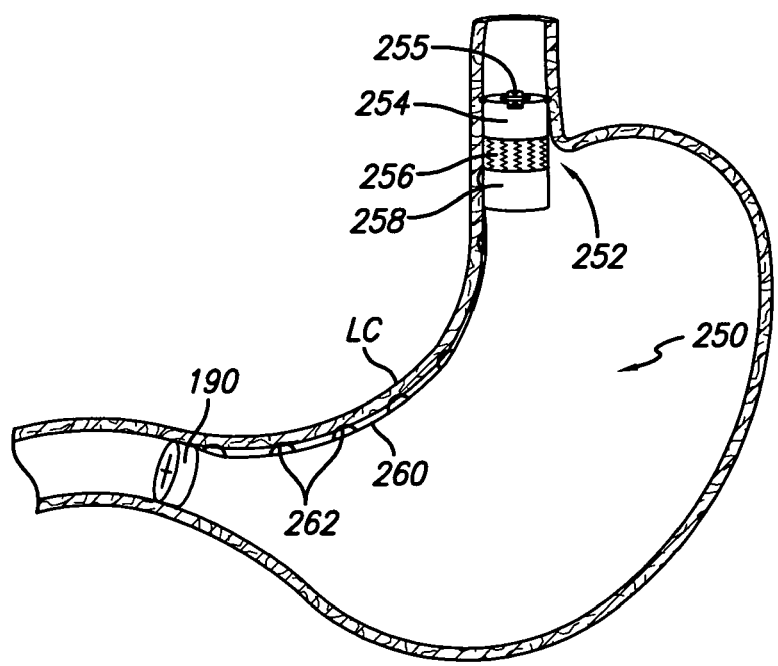
FIG. 23 depicts a schematic view of yet another embodiment of a gastric device attached to the lesser curve of the stomach cavity.

In another embodiment shown in FIG. 23, a gastric device 250 is shown which includes a spring-loaded restrictive element 252, which provides constant pressure at the gastro-intestinal junction. The constant pressure from the spring-loaded restrictive element provides a seal at the gastro-intestinal junction, so that food must enter through the restrictive element, rather than go around it. The spring-loaded restrictive element includes a sealing gasket 254 having a stoma 255 of a desired size, that is positioned on a spring element 256, to continually push the sealing gasket upward or proximally toward the esophagus. The spring element is implanted such that it is normally under compression to provide the upward force necessary to maintain a seal around the gastro-intestinal junction. In one embodiment, the spring element may take the form of a supported fabric structure (i.e., wire covered with PTFE or PET fabric) or may take the form of a bellows, or the like. The spring-loaded restrictive element also includes a docking station 258, which allows for adjustment of the size of the stoma, similar to the docking station 202 described above. Interchangeable sealing gaskets may be used to selectively change the stoma size. It should be noted that the docking station may be incorporated into the spring element or the sealing gasket. The gastric device 250 of this embodiment also includes a spine 260 attached at one end to the docking station, and the spine is used to attach the device along the lesser curve LC of the stomach. Attachment points or clips 262 may be incorporated into the spine or be placed separately around the spine, so as to attach the spine to the lesser curve. Optionally, the spine length may be adjustable to account for various patient geometries. A pressure relief valve 190 may also be included into the gastric device and attached to one end of the spine. As previously described, the pressure relief valve is designed to slow gastric emptying. The valve is designed such that the pressure required to open it is greater than the pressure required to open the pyloric valve. In one embodiment the sealing gasket and the pressure relief valve are expandable members that ratchet open upon an applied internal force (e.g., a balloon). Alternatively, the sealing gasket and the pressure relief valve are self-expanding.

Yet another embodiment of an adjustable gastric system 270 is shown in FIGS. 24 through 26, which may prevent a patient from drinking large volumes and from eating slowly all day. The adjustable gastric system includes fabric or mesh cylindrical body 272 having an inlet 274 at a first end 276 and an outlet 278 at a second end 280. Attachment points or eyelets 281 are disposed at or near the first end of the cylindrical body for passing staples, anchors, or sutures there through to attach the system to the stomach wall near the gastro-intestinal junction. A tensioning member or suture 282 is attached to the cylindrical body in a purse-string fashion between the first and second ends. The suture includes two free ends 284 that are joined with a mechanically adjustable clip 285. A pressure relief valve 286 is attached at the second end of the body blocking the outlet. The pressure relief valve is similar to the pressure relief valve 190 described above, and may be the valve 70, the duckbill or double duckbill valve 100 or 114, the slitted diaphragm valve 130, or the flapper valve 160. Once the gastric system is secured to the stomach wall, the free ends of the suture may be pulled or tensioned to reduce the inner diameter of the cylindrical body, forming a stoma 288 as shown in FIG. 25. The adjustable clip is used to secure the free ends of the suture in position to maintain the desired size of the stoma. At any time the stoma may be adjusted by loosening the clip and either tensioning the suture to further decrease the size of the stoma, or releasing tension of the suture to increase the size of the stoma. The pressure relief valve is such that water may pass freely, but higher-viscosity fluids, such as shakes, can not pass freely. Thus, as the patient drinks a shake, it passes through the stoma but not through the pressure relief valve. The adjustable gastric system will subsequently start to fill up with the shake until it backs up through the stoma and into a pouch 290 that is created above the purse-string suture as shown in FIGS. 25 and 26. The pressure relief valve can be designed to open or partially open at any given pressure, but it is likely that it will open at a pressure that allows the device to back-fill up to or slightly above the first end of the cylindrical body. This same system applies to patients eating slowly throughout the day.

Referring now to FIGS. 27 through 29, another embodiment of the adjustable gastric system 270 is shown including a spine 292 that is connected to the fabric/mesh cylindrical body 272 at the first end 276 and at the second end 280. The spine includes attachment clips 294 that are shown in an open configuration in FIG. 27. During placement of the system within the stomach cavity, the spine allows for attachment of the gastric system to the lesser curve LC of the stomach. Once in position along the lesser curve, the attachment clips are crimped into a closed configuration as best shown in FIG. 28 to secure the spine to the lesser curve. The spine provides column strength, holds the system in place to prevent twisting and/or kinking, and provides additional attachment points to facilitate a more durable implantation.

Another embodiment of the adjustable gastric system 270 is shown in FIG. 30. In this embodiment, a spring element 296 is attached to the fabric/mesh cylindrical body 272 above the purse-string suture 282. Spring element 296 may be formed of multiple coiled wires or wires that are folded in a "zig-zag" pattern along their length, and secured to the valve body at the mouth of the valve, and at least one other portion of the valve spaced longitudinally from the mouth of the valve. The spring elements may be formed of a biocompatible resilient material, such as stainless steel, Elgiloy, NiTi, or a more flexible and conforming material such as silicone, chronoprene, C-Flex, or urethane. This spring-loaded system is implanted in a compressed configuration to apply upward pressure at the gastro-intestinal junction for purposes of an improved seal. The seal caused by the spring element ensures that food enters the inlet 274 of the system, rather than going around the inlet and may also reduce the number of attachment points required at the gastro-intestinal junction.

Another embodiment of an adjustable gastric system 300 is shown in FIG. 31. This system 300 includes fabric or mesh cylindrical body 302 having an inlet 304 at a first end 306 and an outlet 308 at a second end 310. Attachment points or eyelets 311 are disposed at or near the first end of the cylindrical body for passing staples, anchors, or sutures there through to attach the system to the stomach wall near the gastro-intestinal junction. A docking station 312, similar to the docking station 202 described above, is attached to the cylindrical body between the first and second ends, and allows for interchangeable stoma devices 314, similar to the stoma device 210 described above, to be placed. The stoma device includes a stoma 315 that may have a constant diameter or a tapered configuration to encourage food downward and into the device. A pressure relief valve 316 is attached at the second end of the body blocking the outlet. The pressure relief valve is similar to the pressure relief valve 190 described above, and may be the valve 70, the duckbill or double duckbill valve 100 or 114, the slitted diaphragm valve 130, or the flapper valve 160. The pressure relief valve can be designed to open or partially open at any given pressure, but it is likely that it will open at a pressure that allows the device to back-fill up to or slightly above the first end of the cylindrical body.

FIG. 32 shows another embodiment of the adjustable gastric system 300 shown in FIG. 31, including a spine 318 that is connected to the fabric/mesh cylindrical body 302 at least to the first end 306 and at the second end 310. The spine includes attachment clips 320 that are shown in an open configuration in FIG. 32. During placement of the system within the stomach cavity, the spine allows for attachment of the gastric system to the lesser curve LC of the stomach. Once in position along the lesser curve, the attachment clips are crimped into a closed configuration to secure the spine to the lesser curve. The spine provides column strength, holds the system in place to prevent twisting and/or kinking, and provides additional attachment points to facilitate a more durable implantation.

In certain embodiments, fixation devices could be used to secure the valves (70, 100, 114, 130, 160, 190 and 192), tube (50) and isolation elements (194 and 226), spines (242, 260, 292 and 318), and adjustable gastric systems (270 and 300) along the stomach wall. For instance, the system shown having a folder assembly and a fixation assembly as disclosed in U.S. Ser. No. 10/773,883 ("the '883 application"), titled "Single Fold System For Tissue Approximation And Fixation," could be adopted to secure the above-listed devices along the stomach wall. The '883 application is hereby incorporated by reference in its entirety. The system disclosed in the '883 application is used to create single fold plications within the stomach cavity by acquiring a fold of tissue and then deploying multiple staples sequentially or simultaneously in an organized fashion. Another device that could also be used to secure the above-listed devices along the stomach wall is disclosed in U.S. Ser. No. 10/797,439 ("the '439 application"), titled "Devices And Methods For Placement Of Partitions Within A Hollow Body Organ." The '439 application is hereby incorporated by reference in its entirety. The tissue acquisition and fixation device disclosed in the '439 application is used to create longitudinal dual fold plications within the stomach wall, by acquiring two folds of tissue and then stapling the folds together.

In use, the device of the '883 application or the '439 application can be altered so that as the fixation device acquires stomach tissue, a portion of the cylindrical body of the valve (70, 100, 114, 130, 160, 190 and 192) would also be acquired by the fixation device. In some embodiments, the valve includes a fabric/mesh band attached to the cylindrical body as shown in FIG. 12, that may be secured within a fold or dual fold of stomach tissue by the device of the '883 application or the '439 application. When attaching the spine (242, 260, 292 and 318) to the lesser curve of the stomach cavity, the device of the '883 application or the '439 application could be altered to acquire the spine along with the fold(s) or stomach tissue along the lesser curve. With the device of the '439 application, the spine could be positioned and secured in between the dual folds. The device of the '883 application or the '439 application could be actuated multiple times to secure the spine along the entire lesser curve of the stomach. The adjustable gastric system (270 and 300) can also be secured to the stomach using the device of the '883 application or the '439 application, by acquiring at least a portion of the fabric/mesh body near the first and/or second ends of the cylindrical body along with the fold(s) of stomach tissue.

Further, other gastric devices from those disclosed above can be attached to the stomach wall using the device of the '883 application or the '439 application. For instance, several embodiments of the "pouch" disclosed in U.S. Pat. No. 6,845,776 can be secured to the stomach wall using either the device of the '883 application or the '439 application. U.S. Pat. No. 6,845,776 is hereby incorporated by reference in its entirety. Also, the "restrictive device" disclosed in PCT/US2004/009269 could be secured to the stomach wall using the device of the '883 application or the '439 application. PCT/US2004/009269 is hereby incorporated by reference in its entirety. One other example includes the "stoma device" or "anchoring ring" disclosed in U.S. Ser. No. 10/698,148, which could also be secured to the stomach wall using the device of the '883 application or the '439 application. U.S. Ser. No. 10/698,148 is hereby incorporated by reference in its entirety.

In another embodiment, the balloon liner 20, balloon device 40, the valves 70, 100, 114, 130, 160, 190 and 192, tube 50 and isolation element 194 and 226, gastric devices 200, 250, 270 and 300, can all be used in combination with local drug delivery to influence satiety and absorption of nutrients. In one embodiment, a "pump and reservoir" and "active agent catheter delivery system," which are disclosed in U.S. Ser. No. 10/890,340, can be implanted within the patient's body to deliver drugs to the lower gastrointestinal tract while the devices disclosed above can be used to slow gastric emptying or restrict the entrance of food into the stomach cavity.

Figure 33:
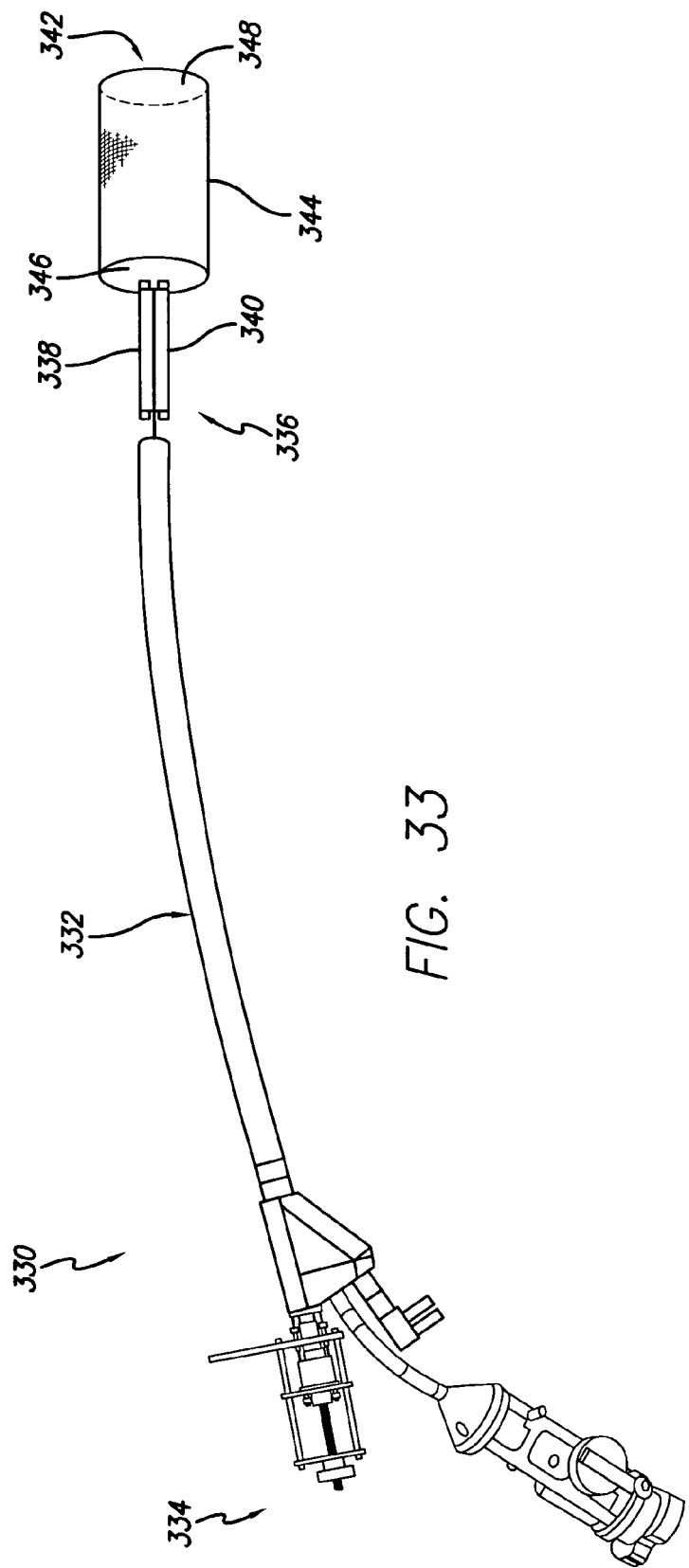
FIG. 33 depicts a liner being loaded onto a tissue acquisition and fixation device.

Another embodiment of a method for placing a liner within the stomach cavity is shown in FIGS. 33 through 37. FIG. 33 shows the tissue acquisition and fixation device 330 having a flexible shaft 332 connected to a handle 334 at one end and a working portion 336 at the other end. A physician can use the handle to steer or control the flexible shaft and actuate the working portion. The working portion includes a cartridge member 338 for holding and dispensing a plurality of staples or anchors, and an anvil member 340. The anvil member is in apposition to the cartridge member and is used to provide a staple closure surface when tissue to be affixed is adequately positioned between the staple cartridge and the anvil. FIG. 33 also shows a liner 342 that is loaded onto the working portion of the tissue acquisition and fixation device to an insertion diameter. A sheath (not shown) may be used to hold the liner at the working portion. The liner may be held against the working portion by any other means, such as by folding and holding the liner between the cartridge member and anvil of the working portion. The liner includes a cylindrical body 344 having an inlet end 346 and an outlet end 348. Depending on the embodiment, the liner may be formed of PET, Nylon, polyester, PTFE, polyethylene, polystyrene, polyurethane, silicone, polyethylene terephthalate, or the like.

Figure 34:
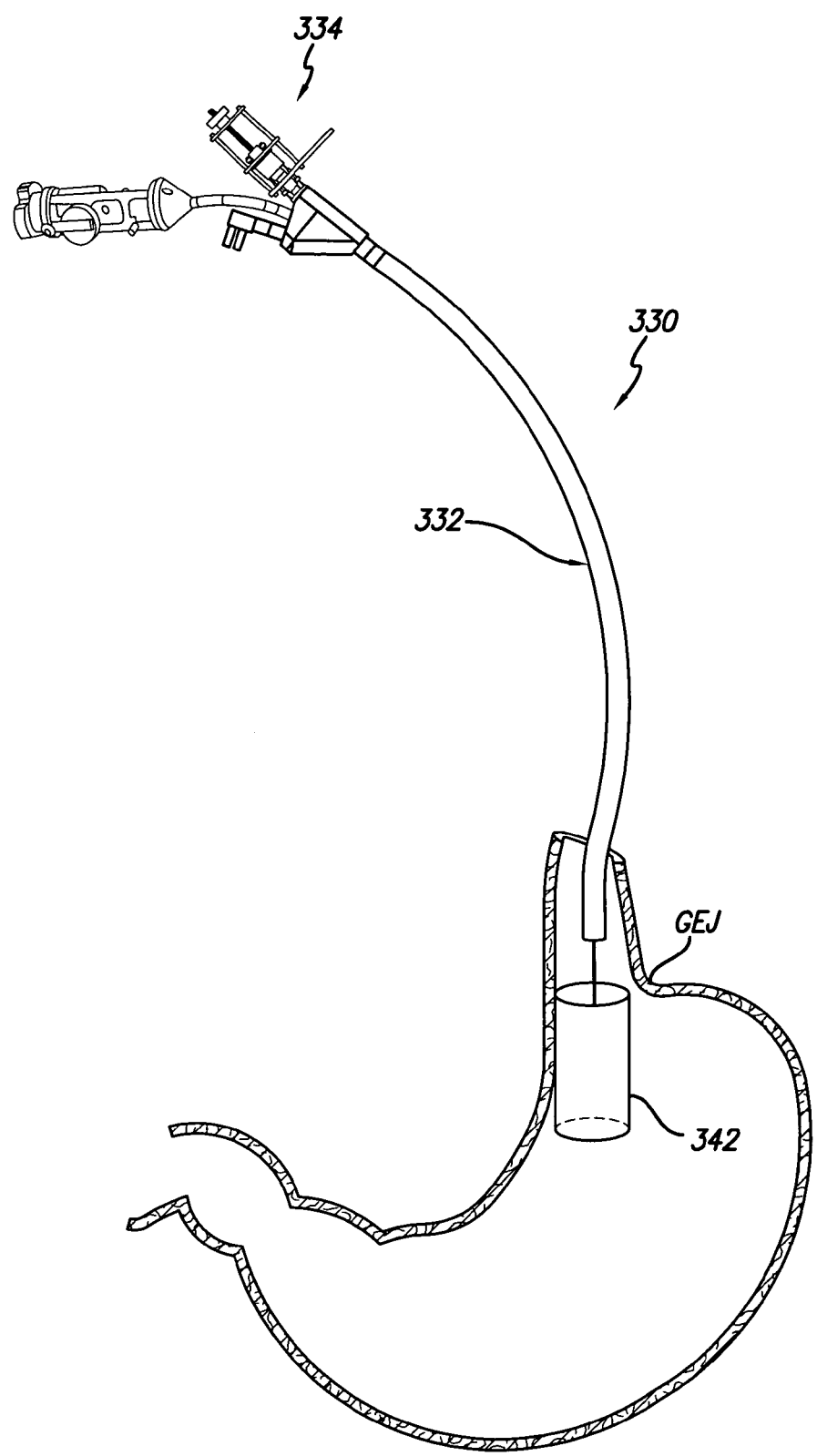
FIG. 34 depicts the liner being positioned with the tissue acquisition and fixation device just below the gastroesophageal junction.

Referring now to FIG. 34, once the liner 342 is loaded on the working portion 336 of the tissue acquisition and fixation device 330, the distal end of the device carrying the liner is inserted transorally until the inlet end 346 of the liner is located just below the GEJ. With the liner in the desired position within the stomach cavity, the working portion of the tissue acquisition and fixation device is actuated, as disclosed in the '439 application, to acquire a dual fold of tissue and the body 344 of the liner. In another embodiment, the tissue acquisition and fixation device may acquire a single fold. After acquiring the tissue and the liner, the cartridge member 338 and anvil member 340 are clamped together, and a plurality of staples are ejected into the tissue and the liner, thereby fixing the liner to the stomach wall. The working portion of the tissue acquisition and fixation device is then repositioned at another point around the circumference of the liner near the inlet end, and that point of the liner is then fixed to a single or dual fold of the stomach wall. Multiple plications 350 may be formed around the circumference of the liner near the inlet end of the body to secure the liner to the stomach wall.

Figure 35:
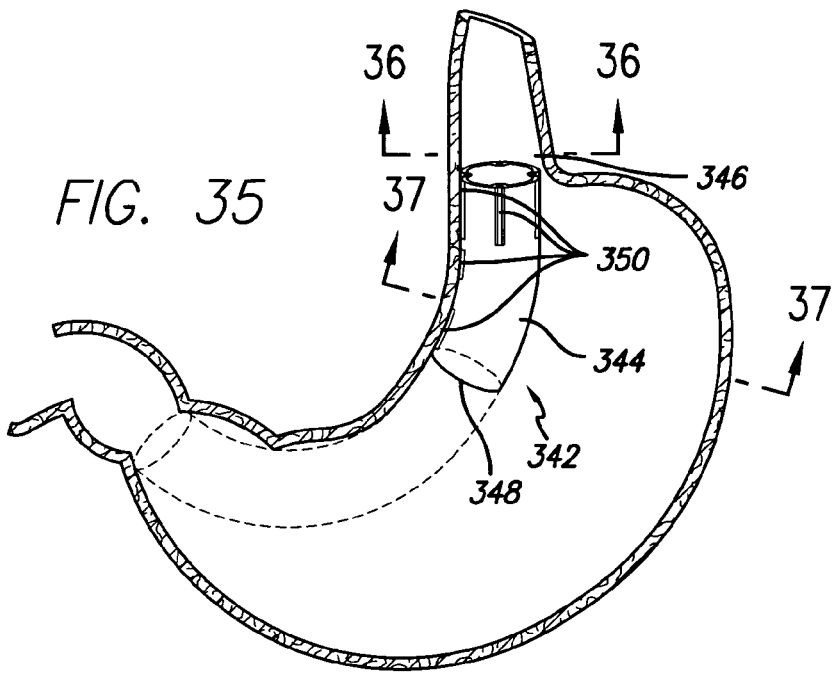
FIG. 35 depicts the liner secured near the gastroesophageal junction and along the lesser curve of the stomach with multiple plications.
Figure 36:
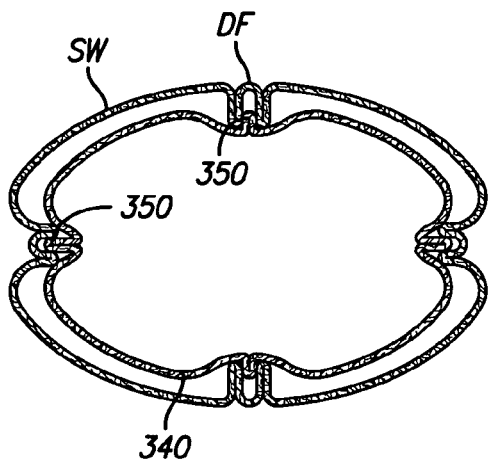
FIG. 36 depicts a cross-sectional view taken along line 36-36 of the FIG. 35.
Figure 37:
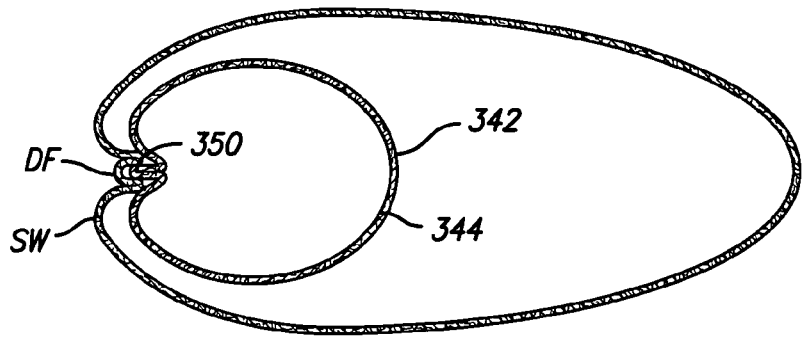
FIG. 37 depicts a cross-sectional view taken along line 37-37 of the FIG. 35.

Once the proximal end or inlet end 346 of the liner 342 is secured to the stomach wall, the tissue acquisition and fixation device 330 is advanced downward or distally towards the distal end or outlet end 348 of the liner as shown in FIG. 35. The tissue acquisition and fixation device is then actuated to place dual or single fold plications 350 along the lesser curve LC of the stomach until the liner is sufficiently anchored to the stomach wall. In other embodiments, the cylindrical body 344 of the liner may extend to the pylorus, and longitudinal plications would be placed all the way down the lesser curve to the pylorus, securing the liner with the dual or single folds of tissue. FIG. 36 shows a cross-sectional view taken along line 36-36 of FIG. 35, showing multiple plications 350 securing the liner 343 within dual folds DF of the stomach wall SW near the GEJ. Referring to FIG. 37, a cross-sectional view taken along line 37-37 of FIG. 35, showing a longitudinal plication 350 securing the liner to the lesser curve of the stomach.

Although the present invention has been described in terms of certain preferred embodiments, other embodiments that are apparent to those of ordinary skill in the art are also within the scope of the invention. Accordingly, the scope of the invention is intended to be defined only by reference to the appended claims. While the dimensions, types of materials described herein are intended to define the parameters of the invention, they are by no means limiting and are exemplary embodiments.

We claim:

1. A method for treatment of a stomach cavity, comprising:
    positioning a tubular liner having a central lumen and proximal and distal ends within the stomach cavity such that the proximal end is adjacent the gastroesophageal junction;
    acquiring first and second folds of tissue and the liner using a fixation device, and plicating the first fold of tissue, the second fold of tissue, and the liner to fix the proximal end of said tubular liner to the stomach wall adjacent the gastroesophageal junction; and
    acquiring third and fourth folds of tissue and the liner using the fixation device, and plicating the third fold of tissue, the fourth fold of tissue, and the liner to fix the distal end of said tubular liner to the stomach wall adjacent the pylorus.

2. The method of claim 1, further comprising fixing at least a portion of the tubular liner within a dual fold of tissue along the lesser curve of the stomach cavity.

3. The method of claim 1, further comprising fixing the tubular liner within folds of tissue a plurality of times along the lesser curve of the stomach cavity.

4. The method of claim 1, wherein the tubular liner includes a cylindrical body with a central lumen in communication with an inlet end and an outlet end, the inlet end being in communication with the esophagus, and further comprising fixing at least a portion of the cylindrical body of the tubular liner within a fold of tissue along the lesser curve of the stomach cavity.

5. The method of claim 4, further comprising attaching a first valve near the inlet end of the tubular liner and attaching a second valve near the outlet end of the tubular liner.

6. The method of claim 1, further comprising fixing a plurality of points around a circumference of the tubular liner between dual folds of tissue in the stomach cavity.

7. The method of claim 1, wherein plicating the proximal and distal_ends of the tubular liner is achieved with staples, sutures, rivets, grommets or adhesive.

8. The method of claim 1, the tubular liner includes a spine with a first end and a second end and a first valve attached to the first end of the spine, and further comprising fixing at least a portion of the spine within a fold of tissue along the lesser curve of the stomach cavity.

9. The method of claim 8, wherein, the tubular liner includes a second valve attached to the second end of the spine, the first valve being positioned near the gastroesophageal junction and the second valve being positioned near the pyloric valve.

10. The method of claim 1, further comprising using a sheath to hold the tubular liner.

11. The method of claim 1, further comprising selecting a tubular liner manufactured from at least one of a group comprising PET, Nylon, polyester, PTFE, polyethylene, polystyrene, polyurethane, silicone, and polyethylene terephthalate.

* * * * *